(12) United States Patent
Wei et al.

(10) Patent No.: US 8,232,098 B2
(45) Date of Patent: *Jul. 31, 2012

(54) P49/STRAP IS A NOVEL PROTEIN INVOLVED IN GENE REGULATION AND CELL PROLIFERATION

(75) Inventors: Jeanne Y. Wei, Little Rock, AR (US); Xiaomin Zhang, Little Rock, AR (US)

(73) Assignees: The Board of Trustees of the University of Arkansas, Little Rock, AR (US); The United States of America as represented by the Department of Veterans Affairs, Washington, DC (US)

( * ) Notice: Subject to any disclaimer, the term of this patent is extended or adjusted under 35 U.S.C. 154(b) by 648 days.

This patent is subject to a terminal disclaimer.

(21) Appl. No.: 12/283,347

(22) Filed: Sep. 11, 2008

(65) Prior Publication Data
US 2009/0035850 A1 Feb. 5, 2009

Related U.S. Application Data

(60) Continuation of application No. 11/726,699, filed on Mar. 22, 2007, now Pat. No. 7,498,411, which is a division of application No. 11/225,270, filed on Sep. 13, 2005, now Pat. No. 7,211,427.

(60) Provisional application No. 60/610,070, filed on Sep. 15, 2004.

(51) Int. Cl.
*C12N 15/00* (2006.01)
*C07H 21/02* (2006.01)
(52) U.S. Cl. .................... 435/320.1; 536/23.1
(58) Field of Classification Search ............... 536/23.1; 435/69.1, 252.3, 320.1
See application file for complete search history.

(56) References Cited

U.S. PATENT DOCUMENTS
2003/0215803 A1  11/2003  Garcia et al.
2004/0101874 A1  5/2004  Ghosh et al.

FOREIGN PATENT DOCUMENTS
CN  360051  7/2002

OTHER PUBLICATIONS

Argentin, S., Ardati, A., Tremblay, S., Lihrmann, I., Robitaille, L., Drouin, J. & Nemer, M. (1994) Developmental stage-specific regulation of atrial natriuretic factor gene transcription. *Mol Cell Biol* 14, 777-90.
Belaguli, N. S., Sepulveda, J. L., Nigam, V., Charron, F., Nemer, M. & Schwartz, R. J. (2000) Cardiac tissue enriched factor serum response factor and GATA-4 are mutual coregulators. *Mol Cell Biol* 20, 7550-8.
Chang, S.H., Poser, S, & Xia, Z. (2004) A novel role for serum response factor in neuronal survival. *Neurosci.* 24, 2277-85.
Chen, F., Kook, H., Milewski, R., Gitler, A. D., Lu, M. M., Li, J., Nazarian, R., Schnepp, R., Jen, K., Biben, C., Runke, G., Mackay, J. P., Novotny, J., Schwartz, R. J., Harvey, R. P., Mullins, M. C. & Epstein, J. A. (2002) Hop is an unusual homeobox gene that modulates cardiac development. *Cell* 110, 713-23.
Du, K. L., Ip, H. S., Li, J., Chen, M., Dandre, F., Yu, W., Lu, M. M., Owens, G. K. & Parmacek, M. S. (2003) Myocardin is a critical serum response factor cofactor in the transcriptional program regulating smooth muscle cell differentiation. *Mol Cell Biol* 23, 2425-37.
Groisman, R., Masutani, H., Leibovitch, M. P., Robin, P., Soudant, I., Trouche, D. & Harel-Bellan, A. (1996) Physical interaction between the mitogen-responsive serum response factor and myogenic basic-helix-loop-helix proteins. *J Biol Chem* 271, 5258-64.
He, T.-C. et al. (1998) A simplified system for generating recombinant adenoviruses. *Proc. Natl. Acad. Sci. USA* 95, 2509-2514.
Helfand, S. L. & Inouye, S. K. (2002) Rejuvenating views of the aging process. *Nat Rev Genet* 3, 149-53.
Johansen, F. E. & Prywes, R. (1994) Two pathways for serum regulation of the c-fos serum response element require specific sequence elements and a minimal domain of serum response factor. *Mol Cell Biol* 14, 5920-28.
Johansen, F. E. & Prywes, R. (1993) Identification of transcriptional activation and inhibitory domains in serum response factor (SRF) by suing GAL4-SRF constructs. *Mol Cell Biol* 13, 4640-47.
Koppe, M.J. et al., (2004) Biodistribution and threapeutic efficacy of . . . labeled monoclonal antibody MN-14 to carcinoembryonic antigen in mice with small peritoneal metastases of colorectal origin. *J. Nucl. Med.* 45, 1224-1232.
Li, X, Rosenfeld MG. (2004) Origins of licensing control. *Nature* 427(6976), 687-8.
Miano, J. M. (2003) Serum response factor: toggling between disparate programs for gene expression. *J Mol Cell Cardiol* 35, 577-93.
Morin, S., Paradis, P., Aries, A. & Nemer, M. (2001) Serum response factor-GATA ternary complex required for nuclear signaling by a G-protein-coupled receptor. *Mol Cell Biol* 21, 1036-44.
Thuerauf, DJ, Arnold ND, Zechner D, Hanford DS, DeMartin KM, McDonough PM, Prywes R, Glembotski CC. (1998) p38 mitogen-activated protein kinase mediates the transcriptional induction of the atrial natriuretic factor gene through a serum response element.*J Biol Chem* 273(32):20636-43.
Treisman, R. (1992) The serum response element. *Trends Biochem Sci* 17, 423-6.
Tsou, H., Azhar, G., Lu, X. G., Kovacs, S., Peacocke, M. & Wei, J.Y. (1996) Age-associated changes in basal c-fos transcription factor binding activity in rat hearts. *Exp Cell Res* 229, 432-7.
Vaitkevicius, PV, Lane M, Spurgeon H, Ingram DK, Roth GS, Egan JJ, Vasan S, Wagle DR, Ulrich P, Brines M, Wuerth JP, Cerami A, Lakatta EG (2001) A cross-link breaker has sustained effects on arterial and ventricular properties in older rhesus monkeys. *Proc Natl Acad Sci USA* 98(3), 1171-5.
Wang, Z, Wang DZ, Hockemeyer D, McAnally J, Nordheim A, Olson EN. (2004) Myocardin and ternary complex faCtors compete for SRF to control smooth muscle gene expression. *Nature.* 11; 428 (6979): 185-9.

(Continued)

*Primary Examiner* — Maryam Monshipouri
(74) *Attorney, Agent, or Firm* — Hugh McTavish

(57) ABSTRACT

The invention provides isolated p49/STRAP protein, and isolated nucleic acids encoding a p49/STRAP protein. The inventors have discovered a new protein, named p49/STRAP that is expressed in cardiac tissue and other tissues in mammals. The p49/STRAP protein binds to serum response factor (SRF) and regulates transcription of SRF-responsive genes in the heart. p49/STRAP is also discovered to inhibit tumor cell proliferation, and thus the invention provides a method of inhibiting cancer cell proliferation by contacting the cells with p49/STRAP.

3 Claims, 11 Drawing Sheets

OTHER PUBLICATIONS

Wang, D., Chang, P. S., Wang, Z., Sutherland, L., Richardson, J. A., Small, E., Krieg, P. A. & Olson, E. N. (2001) Activation of cardiac gene expression by myocardin, a transcriptional cofactor for serum response factor. *Cell* 105, 851-62.

Wei, JY. (1992) Age and the cardiovascular system. *N Eng J Med* 327(24), 1735-9.

Wycuff, D.R., Yanites, H.L., & Marriott, S.J. (2004) Identification of a functional serum response element in th HTLV-I LTR. *Virology* 324, 540-53.

Zhang, P., Behre, G., Pan, J., Iwama, A., Wara-Aswapati, N., Radomska, H. S., Auron, P. E., Tenen, D. G. & Sun, Z. (1999) Negative cross-talk between hematopoietic regulators. *Proc Natl Acad Sci USA* 96, 8705-10.

Zhang, X., Chai, J., Azhar, G., Sheridan, P., Borras, A. M., Furr, M. C., Khrapko, K., Lawitts, J., Misra, R. P. & Wei, J. Y. (2001) Early postnatal cardiac changes and premature death in transgenic mice overexpressing a mutant form of a serum response factor. *J Biol Chem* 276, 40033-40.

Zhang, X., Azhar, G., Furr, M. C., Zhong, Y. & Wei, J. Y. (2003) Model of functional cardiac aging: young adult mice with mild overexpression of serum response factor. *Am J Physiol Regul Integr Comp Physiol* 285, R552-60.

Zhang, X., Azhar, G., Chai, J., Sheridan, P., Nagano, K., Brown, T., Yang, J., Khrapko, K., Borras, A. M., Lawitts, J., Misra, R. P. & Wei, J.Y. (2001) Cardiomyopathy in transgenic mice with cardiac-specific overexpression of serum response factor. *Am J Physiol Heart Circ Physiol* 280, H1782-92.

Strausberg, RL et al., 2002. Generation and initial analysis of more than 15,000 full-length human and mouse cDNA sequences. Proc. Natl. Acad. Sci. USA 99:16899-16903.

Ishibashi et al., GenEmbl Database, Accession No. AK058015, Sep. 2003.

Fig. 1

```
Mouse       1   MAADPLPPSAMVQPGTLNLNNEVVKMRKEVKRIRVLVIRKLVRSVGRLKSKKGTEDALLK
Human       1           MAQPGTLNLNNEVVKMRKEVKRIRVLVIRKLVRSVGRLKSKKGTEDALLK
Consensus       *   ************************************************

Mouse       61  NQRRAQRLLEEIHAMKELKPDVVTKSALSDDINFEKTCKKPDSTATDRAVARLAGHPLLK
Human       51  NQRRAQRLLEEIHAMKELKPDIVTKSALGDDINFEKIFKKPDSTATERAIARLAVHPLLK
Consensus       ********************  *****  ******  ****  ********  ****   *****

Mouse       121 KKIDVLKDAVQAFKDARQSAPAAESSESTSGEGRCKDIARSKDDARESQHPERTVVREQK
Human       111 KKIDVLKAAVQAFKEARQNVAEVESSKNASEDNHSENTLYSNDNGSNLQR-EAT.ISEQK
Consensus       ******  ******  ***       ***     *          * *      *   * *-   ***

Mouse       181 AKDTNTAAKNAASGSKEKLAKTEQAPRAGTTPGSQGRPSGKGAGVNSEHQGAPAPGDSNQ
Human       170 VKETKILAKKPIHNSKEKIAKMEHGPKAVTIANSPSKPSEKDSVVSLESQKTPAD-PKLK
Consensus        *   ***   ****  **  *    *     *      **  *       *   *   **

Mouse       241 GKASTKTPEDSVCEPANNGVSEEEESEGEKEYFDDSTEERFYKQSSASEDSDSGDDFFIG
Human       229 TLSQTKKNKGSDSSLSGNSDGGEEFCEEEKEYFDDSTEERFYKQSSMSEDSDSGDDFFIG
Consensus         **     *        *    **   *  *******************   *************

Mouse       301 KVRRTRKKESGVHSSAKELKPLPKVPSKTSTLETPWDVRNDKHRPIPEARKFESVFFHSL
Human       289 KVRRTRKKESSCHSSVKEQKPLEKVFLKEDTGETHGDTRNDKIKPSTETRKLESVFSHSL
Consensus       **********   ***  **  ***  **   *    *    *  **   *  ****   *   *  **  ****

Mouse       361 AGPKSSRRDPREQAPKNKAPDFPENEPPVKKQFTKSAYRGFESVKQTMQAPLHPSWEASR
Human       349 SGSKSSRRNFKEQAPKTRSLDFPQNEPQIKNQFNKKLSGRLENTKQQLQLPLHPSWEASR
Consensus        *  ****   *****     ***  ***   *  ***      *    *   **    ***********

Mouse       421 RRKEQQSKIAVFQGKKITFDD 441
Human       409 RRKEQQSNIAVFQGKKNYV    427
Consensus       *******  *********
```

Structure of Ad-p49/strap

SEQUENCE LISTING

```
<160> NUMBER OF SEQ ID NOS: 6

<210> SEQ ID NO 1
<211> LENGTH: 427
<212> TYPE: PRT
<213> ORGANISM: Homo sapiens

<400> SEQUENCE: 1
```

```
Met Ala Gln Pro Gly Thr Leu Asn Leu Asn Asn Glu Val Val Lys Met
1               5                   10                  15
Arg Lys Glu Val Lys Arg Ile Arg Val Leu Val Ile Arg Lys Leu Val
                20                  25                  30
Arg Ser Val Gly Arg Leu Lys Ser Lys Lys Gly Thr Glu Asp Ala Leu
            35                  40                  45
Leu Lys Asn Gln Arg Arg Ala Gln Arg Leu Leu Glu Glu Ile His Ala
        50                  55                  60
Met Lys Glu Leu Lys Pro Asp Ile Val Thr Lys Ser Ala Leu Gly Asp
65                  70                  75                  80
Asp Ile Asn Phe Glu Lys Ile Phe Lys Lys Pro Asp Ser Thr Ala Thr
                85                  90                  95
Glu Arg Ala Ile Ala Arg Leu Ala Val His Pro Leu Leu Lys Lys Lys
            100                 105                 110
Ile Asp Val Leu Lys Ala Ala Val Gln Ala Phe Lys Glu Ala Arg Gln
        115                 120                 125
Asn Val Ala Glu Val Glu Ser Ser Lys Asn Ala Ser Glu Asp Asn His
    130                 135                 140
Ser Glu Asn Thr Leu Tyr Ser Asn Asp Asn Gly Ser Asn Leu Gln Arg
145                 150                 155                 160
Glu Ala Thr Val Ile Ser Glu Gln Lys Val Lys Glu Thr Lys Ile Leu
                165                 170                 175
Ala Lys Lys Pro Ile His Asn Ser Lys Glu Lys Ile Ala Lys Met Glu
            180                 185                 190
His Gly Pro Lys Ala Val Thr Ile Ala Asn Ser Pro Ser Lys Pro Ser
        195                 200                 205
Glu Lys Asp Ser Val Val Ser Leu Glu Ser Gln Lys Thr Pro Ala Asp
    210                 215                 220
Pro Lys Leu Lys Thr Leu Ser Gln Thr Lys Lys Asn Lys Gly Ser Asp
225                 230                 235                 240
Ser Ser Leu Ser Gly Asn Ser Asp Gly Gly Glu Glu Phe Cys Glu Glu
                245                 250                 255
Glu Lys Lys Tyr Phe Asp Asp Ser Thr Glu Glu Arg Phe Tyr Lys Gln
            260                 265                 270
Ser Ser Met Ser Glu Asp Ser Asp Ser Gly Asp Asp Phe Phe Ile Gly
        275                 280                 285
Lys Val Arg Arg Thr Arg Lys Lys Glu Ser Ser Cys His Ser Ser Val
    290                 295                 300
Lys Glu Gln Lys Pro Leu Glu Lys Val Phe Leu Lys Glu Asp Thr Gly
305                 310                 315                 320
Glu Thr His Gly Asp Thr Arg Asn Asp Lys Ile Lys Pro Ser Thr Glu
                325                 330                 335
Thr Arg Lys Leu Glu Ser Val Phe Ser His Ser Leu Ser Gly Ser Lys
            340                 345                 350
Ser Ser Arg Arg Asn Phe Lys Glu Gln Ala Pro Lys Thr Arg Ser Leu
        355                 360                 365
Asp Phe Pro Gln Asn Glu Pro Gln Ile Lys Asn Gln Phe Asn Lys Lys
    370                 375                 380
Leu Ser Gly Arg Leu Glu Asn Thr Lys Gln Gln Leu Gln Leu Pro Leu
385                 390                 395                 400
His Pro Ser Trp Glu Ala Ser Arg Arg Lys Glu Gln Gln Ser Asn
                405                 410                 415
Ile Ala Val Phe Gln Gly Lys Lys Asn Tyr Val
```

420            425

<210> SEQ ID NO 2
<211> LENGTH: 441
<212> TYPE: PRT
<213> ORGANISM: Mus musculus

<400> SEQUENCE: 2

Met Ala Ala Asp Pro Leu Pro Pro Ser Ala Met Val Gln Pro Gly Thr
1               5                   10                  15

Leu Asn Leu Asn Asn Glu Val Val Lys Met Arg Lys Glu Val Lys Arg
            20                  25                  30

Ile Arg Val Leu Val Ile Arg Lys Leu Val Arg Ser Val Gly Arg Leu
        35                  40                  45

Lys Ser Lys Lys Gly Thr Glu Asp Ala Leu Leu Lys Asn Gln Arg Arg
50                  55                  60

Ala Gln Arg Leu Leu Glu Glu Ile His Ala Met Lys Glu Leu Lys Pro
65                  70                  75                  80

Asp Val Val Thr Lys Ser Ala Leu Ser Asp Asp Ile Asn Phe Glu Lys
                85                  90                  95

Thr Cys Lys Lys Pro Asp Ser Thr Ala Thr Asp Arg Ala Val Ala Arg
            100                 105                 110

Leu Ala Gly His Pro Leu Leu Lys Lys Lys Ile Asp Val Leu Lys Asp
        115                 120                 125

Ala Val Gln Ala Phe Lys Asp Ala Arg Gln Ser Ala Pro Ala Ala Glu
130                 135                 140

Ser Ser Glu Ser Thr Ser Gly Glu Gly Arg Cys Lys Asp Ile Ala Arg
145                 150                 155                 160

Ser Lys Asp Asp Ala Arg Glu Ser Gln His Pro Glu Arg Thr Val Val
                165                 170                 175

Arg Glu Gln Lys Ala Lys Asp Thr Asn Thr Ala Ala Lys Asn Ala Ala
            180                 185                 190

Ser Gly Ser Lys Glu Lys Leu Ala Lys Thr Glu Gln Ala Pro Arg Ala
        195                 200                 205

Gly Thr Thr Pro Gly Ser Gln Gly Arg Pro Ser Gly Lys Gly Ala Gly
210                 215                 220

Val Asn Ser Glu His Gln Gly Ala Pro Ala Pro Gly Asp Ser Asn Gln
225                 230                 235                 240

Gly Lys Ala Ser Thr Lys Thr Pro Glu Asp Ser Val Cys Glu Pro Ala
                245                 250                 255

Asn Asn Gly Val Ser Glu Glu Glu Ser Glu Gly Glu Lys Glu Tyr
            260                 265                 270

Phe Asp Asp Ser Thr Glu Glu Arg Phe Tyr Lys Gln Ser Ser Ala Ser
        275                 280                 285

Glu Asp Ser Asp Ser Gly Asp Asp Phe Phe Ile Gly Lys Val Arg Arg
290                 295                 300

Thr Arg Lys Lys Glu Ser Gly Val His Ser Ser Ala Lys Glu Leu Lys
305                 310                 315                 320

Pro Leu Pro Lys Val Pro Ser Lys Thr Ser Thr Leu Glu Thr Pro Trp
                325                 330                 335

Asp Val Arg Asn Asp Lys His Arg Pro Ile Pro Glu Ala Arg Lys Phe
            340                 345                 350

Glu Ser Val Phe Phe His Ser Leu Ala Gly Pro Lys Ser Ser Arg Arg
        355                 360                 365

Asp Pro Arg Glu Gln Ala Pro Lys Asn Lys Ala Pro Asp Phe Pro Glu

```
                370               375               380
Asn Glu Pro Pro Val Lys Lys Gln Phe Thr Lys Ser Ala Tyr Arg Gly
385                 390                 395                 400

Phe Glu Ser Val Lys Gln Thr Met Gln Ala Pro Leu His Pro Ser Trp
                405                 410                 415

Glu Ala Ser Arg Arg Lys Glu Gln Gln Ser Lys Ile Ala Val Phe
                420                 425                 430

Gln Gly Lys Lys Ile Thr Phe Asp Asp
            435                 440

<210> SEQ ID NO 3
<211> LENGTH: 1284
<212> TYPE: DNA
<213> ORGANISM: Homo sapiens

<400> SEQUENCE: 3
atggctcagc cgggaactct gaacctcaat aacgaggttg tgaagatgag aaaagaagtg    60
aagagaattc gagttttagt tatccgaaaa cttgtcagga gtgttggccg actgaagtca   120
aaaaagggta ctgaagatgc actgttaaaa accaaagac gggcgcaaag attgcttgaa   180
gaaatccatg ccatgaagga attgaaacct gacatagtaa ctaaatctgc tcttggtgat   240
gatatcaact ttgaaaaaat cttcaaaaag ccagattcta ctgcaactga agagcaatt   300 gccagactag cagtacatcc tcttctgaag aaaaagatag atgtgctaaa agctgctgta   360
caagccttta agaagcaag acaaaatgtt gctgaagttg agtcatcaaa gaatgcttca   420
gaggacaatc attctgagaa tactttgtat tcaaatgata atggaagtaa tttacagcgt   480
gaagcaactg tcatcagtga gcaaaaagtc aagagaaacca aaatattggc gaagaaacca   540
atacataatt caaaggaaaa aatagcaaag atggaacatg acctaaagc agtgactatt   600 gcaaattctc catcaaagcc ttcagaaaag gattctgtag tttcccttga gtcccagaag   660
acacctgctg acccaaaaact gaaaactcta agtcaaacca aaaaaaacaa aggatctgat   720
agctcactct ctggtaacag tgatggcgga gaagaattt gtgaagagga aagaaatat   780 tttgatgata gcacagaaga aaggttttac aagcagtctt ccatgtctga agatagtgat   840
agcggtgacg acttcttcat tgggaaagtc agacggacac gaaagaagga agtagttgt   900 cattcttcag ttaaggaaca aaaaccacta gaaaaagtgt tcttaaaga agatacaggt   960 gaaactcatg gggatacaag aaatgacaaa atcaagccaa gtacagaaac cagaaagtta  1020
gaatcagtgt tttcccactc tttatctgga tctaaaagct ctagaagaaa tttcaaagaa  1080
caggctccaa aaacaagatc cctagatttt ccacagaatg agcctcagat caagaatcag  1140
tttaataaga agctatcagg aagacttgaa aatacaaaac agcaattgca gctgcctctt  1200
catccttcat gggaagcaag cagaaggcga aagaacagc aatctaatat tgctgtgttt  1260
caggggaaaa aaaattacgt ttga                                          1284

<210> SEQ ID NO 4
<211> LENGTH: 1326
<212> TYPE: DNA
<213> ORGANISM: Mus musculus

<400> SEQUENCE: 4
atggcggctg accctcttcc tccgtccgca atggttcagc cggggactct gaacctcaat    60
aacgaggttg taagatgag aaaagaagtg aagcgaatcc gagttctggt catccgaaaa   120
cttgtcagga gtgtcggcag actgaagtcc aaaaagggca cagaagatgc actgttgaaa   180
```

```
aaccaaaggc gagcccaaag gttgcttgag gagatccatg ccatgaagga attgaaacct    240
gatgttgtaa ctaaatctgc tcttagtgat gatatcaact ttgaaaaaac ttgcaaaaag    300
ccggattcta ccgcgactga cagagcggtt gccagattag caggtcaccc gcttctgaag    360
aagaaaattg atgtgctaaa agatgctgtc caggccttca aagatgcaag gcagagtgct    420
ccagcggccg aatcatctga gagtacttca ggagaaggcc ggtgtaagga cattgcaagg    480 tcaaaggat atgcacgtga gtcacagcat cctgagagaa ctgttgtcag ggagcagaag    540
gcaaaggaca ccaacacggc agcaaagaat gcagcaagtg gttcaaaaga aaaactggcc    600
aagacagagc aggcacccag agcagggacc actccagggt ctcaggggag gccttcagga    660
aagggtgctg gggttaactc tgaacaccag ggggcccag ccccaggga cagcaaccag    720 gggaaagcct caaccaaaac cccggaggac agcgtgtgtg aacctgctaa taacggtgtc    780
agtgaggaag aggagagcga gggggaaaag gagtattttg atgacagcac tgaagaacgg    840
ttctacaaac agtcttctgc atctgaggac agcgacagtg gtgacgactt cttcattgga    900
aaagtcagac ggactcgaaa gaaggaatct ggtgtccatt cctcggccaa ggaactgaag    960
cccctcccaa aggtaccatc taaaacaagt acacttgaaa ccccctggga tgtaagaaac   1020
gataaacaca ggccaattcc agaagccagg aagttcgaat ccgtgttttt ccactcgttg   1080
gctggaccta aaagctccag aagggatccc agagaacagg ccccaaagaa taaagcccca   1140
gattttccag aaaatgaacc cccagtcaag aagcagttta caaagagtgc atacagaggc   1200
tttgagagtg tgaagcagac gatgcaggca cctctgcatc cgtcctggga agcgagcagg   1260
aggcggaagg agcagcagtc caaaatcgct gtgtttcagg ggaaaaaaat tacatttgat   1320
gattga                                                              1326

<210> SEQ ID NO 5
<211> LENGTH: 18
<212> TYPE: PRT
<213> ORGANISM: Homo sapiens

<400> SEQUENCE: 5

Lys Ser Lys Lys Gly Thr Glu Asp Ala Leu Leu Lys Asn Gln Arg Arg
1               5                   10                  15

Ala Gln

<210> SEQ ID NO 6
<211> LENGTH: 22
<212> TYPE: DNA
<213> ORGANISM: Mus musculus

<400> SEQUENCE: 6
ggatgtccat attaggacat ct                                              22
```

P49/STRAP IS A NOVEL PROTEIN INVOLVED IN GENE REGULATION AND CELL PROLIFERATION

PRIORITY

This application is a continuation of U.S. utility patent application Ser. No. 11/726,699, filed Mar. 22, 2007, now U.S. Pat. No. 7,498,411, which is a divisional of U.S. utility patent application Ser. No. 11/225,270, filed Sep. 13, 2005, now U.S. Pat. No. 7,211,427, which claims priority to U.S. provisional patent application Ser. No. 60/610,070, filed Sep. 15, 2004, titled Serum Response Factor (SRF) Cofactor Involved in Cardiac Gene Regulation.

GOVERNMENT SUPPORT

This invention was made with government support under grants AG18388 and AG19946 awarded by the United States Department of Health and Human Services and with funding by the Central Arkansas Veterans Healthcare System (CAVHS). The government has certain rights in the invention.

BACKGROUND OF THE INVENTION

Cardiac disease is one of the leading causes of death in the United States. The incidence of cardiac disease increases rapidly with advancing age.

It is well appreciated that the mammalian adult heart undergoes a number of changes with advancing age (1-3). Recent studies indicate that one of the key transcription factors in muscle and other tissues, serum response factor (SRF), is implicated in the regulation of cardiac genes during development and during adult aging (4-7). SRF is a member of the MADS (MCM1, Agamous, Deficiens, SRF) family of transcription factors that regulates a number of immediate-early and muscle-specific genes, and also serves to regulate cell proliferation, cell size, and cell survival (4-11). SRF forms dimers and recruits SRF cofactors or SRF binding proteins when it binds to the serum response element (SRE), which is located in the promoter region of each of its target genes (8-12). SRF is highly expressed in the heart during embryonic and early postnatal development, and it is mildly increased by approximately 20% from post-maturational adulthood to senescence (4-7, 12). The mRNA levels of a number of SRF target genes, including atrial natriuretic factor (ANF), alpha-myosin heavy chain (α-MHC), and sarcoplasmic reticular calcium ATPase (SERCA2), have also been reported to undergo changes during early postnatal cardiac development and during senescence (4-7, 12-14). In a transgenic mouse model in which the human SRF gene was mildly overexpressed in the heart, cardiac changes resembling those that have been observed during adult aging in terms of myocardial function, morphology, and gene expression were observed in young adulthood (7). The mildly increased cardiac-specific SRF expression apparently up-regulates some SRF target genes while it down-regulates others in the heart (7). This bidirectional pattern of altered gene expression following mild SRF up-regulation suggests that possibly other transcription regulators, including perhaps certain SRF cofactors, may pose either positive and/or negative modulatory effects on the activation of SRF target genes (7, 14-18). These other proteins and/or cofactors may also modulate SRF in its ability to regulate cell growth and proliferation (4-11).

SRF has been reported to exhibit functional interactions with a number of SRF cofactors and/or binding proteins in the regulation of SRF target genes (15-17). These interactions likely modulate SRF function and may also enable SRF to mediate tissue-specific regulation at different developmental stages (18-20). To date, a number of SRF cofactors, including the TCF family of proteins, the SAP protein myocardin, Nkx 2.5, and Hop, have been identified, and their various functions in cardiac development have been investigated (20-23). Fewer studies have reported on the role of SRF cofactors in the regulation of cardiac genes during adult aging and senescence.

New tools to understand the biology of cardiac disease and the changes in the heart that occur with advancing age are needed. Materials useful to screen for genetic susceptibility to heart conditions are needed. Materials useful to reverse or halt some of the changes in the heart that occur in a disease or with advancing age are needed.

Cancer is the second leading cause of death in the United States. New tools and materials to inhibit cancer cell proliferation, treat cancer, and understand cancer biology are also needed.

SUMMARY

The invention is based on the discovery of a new protein found in humans and mice, that we have named p49/STRAP, and the nucleotide sequences that encode it. The protein binds to serum response factor, SRF, a transcription factor found in muscle and other tissue and believed to help regulate cardiac genes in development and adult aging. The protein is 49 kDa and was named p49/STRAP for SRF-dependent Transcription Regulation Associated Protein. Unlike most SRF cofactors, p49/STRAP binds to the COOH terminal portion of SRF, and can simultaneously bind to SRF with another cofactor that binds the NH2-terminal portion of SRF. p49/STRAP was found at high levels in the heart, liver, and kidney in both humans and mice. It was also found in the brain, skeletal muscle, placenta, pancreas, and testis in at least one of the two species. p49/STRAP mRNA was increased in the heart in old humans and mice compared to young adults. p49/STRAP binds to SRF both in vitro and in vivo. It also modulates the transcription of several cardiac genes, particularly in conjunction with SRF, increasing the transcription of some genes and decreasing transcription of at least one gene. In addition, it modulates cell growth and proliferation.

The human p49/STRAP protein is SEQ ID NO:1, and the mouse p49/STRAP protein is SEQ ID NO:2. The human p49/STRAP cDNA is SEQ ID NO:3, and the mouse p49/STRAP cDNA is SEQ ID NO:4.

Thus, the invention provides an isolated peptide or protein that includes 10 or more residues at least 90% identical to a fragment of a p49/STRAP protein, wherein the p49/STRAP protein is SEQ ID NO:1 or SEQ ID NO:2.

Another embodiment of the invention provides an isolated p49/STRAP protein.

Another embodiment of the invention provides an isolated nucleic acid that includes a p49/STRAP gene.

Another embodiment of the invention provides an isolated nucleic acid that includes a fragment of at least 10 nucleotides of a p49/STRAP gene, wherein the p49/STRAP gene is SEQ ID NO:3 or SEQ ID NO:4, or a complement thereof.

Another embodiment of the invention provides an isolated nucleic acid that includes 20 or more nucleotides at least 90% identical to a fragment of a p49/STRAP gene, wherein the p49/STRAP gene is SEQ ID NO:3 or SEQ ID NO:4, or a complement thereof.

Another embodiment of the invention provides an isolated nucleic acid that includes 100 or more nucleotides at least 65% identical to a fragment of a p49/STRAP gene, wherein the p49/STRAP gene is SEQ ID NO:3 or SEQ ID NO:4, or a complement thereof.

Another embodiment of the invention provides a method of identifying a nucleic acid molecule that is related to a p49/STRAP gene involving: (a) hybridizing an isolated nucleic acid comprising a fragment of at least 10 nucleotides of SEQ ID NO:3 or SEQ ID NO:4, or a complement thereof to a nucleic acid sample so as to form a complex with the nucleic acid molecule related to a p49/STRAP gene; and (b) detecting the presence of the complex.

Another embodiment of the invention provides a recombinant host cell containing an isolated nucleic acid that includes a p49/STRAP gene.

Another embodiment of the invention provides a recombinant host cell containing: an isolated nucleic acid that includes a fragment of at least 10 nucleotides of SEQ ID NO:3 or SEQ ID NO:4, or a complement thereof.

Another embodiment of the invention provides a recombinant host cell that expresses from a recombinant nucleic acid molecule a peptide or protein comprising 10 or more residues at least 90% identical to a fragment of a p49/STRAP protein, wherein the p49/STRAP protein is SEQ ID NO:1 or SEQ ID NO:2, or a complement thereof.

Another embodiment of the invention provides an isolated nucleic acid capable of hybridizing to a p49/STRAP gene under hybridization conditions of 6×SSC, 5×Denhardt's, 0.5% SDS, and 100 micrograms/ml fragmented and denatured salmon sperm DNA hybridized overnight at 65° C. and washed two times at room temperature for 10 minutes each in 2×SSC, 0.1% SDS and one time at 55° C. for one hour; wherein the p49/STRAP gene is SEQ ID NO:3 or SEQ ID NO:4.

Another embodiment of the invention provides an antibody that specifically recognizes a p49/STRAP protein, wherein the p49/STRAP protein is SEQ ID NO:1 or SEQ ID NO:2.

Another embodiment of the invention provides a recombinant cell containing an insertion or a deletion in a p49/STRAP gene.

Another embodiment of the invention provides a method of inhibiting proliferation of cancer cells involving contacting the cancer cell with an effective amount of p49/STRAP protein.

The tight binding of p49/STRAP to SRF can also be used to detect SRF. Thus, another embodiment of the invention provides a method of detecting SRF involving contacting a sample suspected of containing SRF with a labeled p49/STRAP or SRF-binding peptide thereof, and detecting the label.

BRIEF DESCRIPTION OF THE FIGURES

FIG. 1 shows an alignment of the mouse (SEQ ID NO:2) and human (SEQ ID NO:1) p49/STRAP protein sequences.

DETAILED DESCRIPTION

Definitions

Figure 2A:
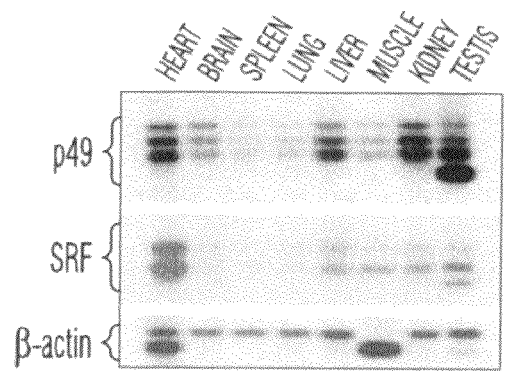
FIGS. 2A-D show expression of p49/STRAP mRNA and protein in mouse and human tissues. 2A: p49/STRAP and SRF mRNA levels in mouse tissues. 2B: p49/STRAP protein levels in mouse tissues. 2C: p49/STRAP and SRF mRNA levels in human tissues. 2D: p49/STRAP and SRF mRNA levels in the fetal and adult human heart, aorta, apex, left atrium (L.A.), right atrium (R.A.), left ventricle (L.V.), and right ventricle (R.V.).

A "p49/STRAP protein," as used herein, refers to a protein that binds in vitro and in vivo to the COOH-terminal portion of SRF, and that has an amino acid sequence at least 40% identical to both SEQ ID NO:1 and SEQ ID NO:2, the human and mouse p49/STRAP sequences respectively. Binding in vitro and in vivo to SRF can be assayed as described in Example 1 below.

Nucleotide and protein sequence identity for segments of complete sequences is calculated using the default BLAST parameters for nucleotide or protein sequence comparison at the BLAST website, www.ncbi.nlm.nih.gov/BLAST/. Nucleotide sequence identity for complete sequences is calculated with alignments at tandem.bu.edu/align.tool.html with the default parameters. Protein sequence identity for alignments of complete protein sequences is calculated using the alignment tool at us.expasy.org/tool/sim-prot.html with the default parameters.

A "p49/STRAP gene" as used herein refers to a nucleic acid, whether RNA or DNA, that encodes a p49/STRAP protein. The p49/STRAP gene may be chromosomal or cDNA, contain introns or not, and include upstream or downstream regulatory sequences or not.

Description

The p49/STRAP protein and nucleic acids encoding it have several uses. First, as shown in Example 2 below, p49/STRAP causes cell cycle arrest and inhibits proliferation of colon cancer cells.

Since the protein is involved in cardiac gene regulation, mutations in the p49/STRAP gene likely cause diseases in cardiac tissue and other tissues where p49/STRAP is expressed. Thus, the nucleic acids can be used to screen for genetic diseases.

p49/STRAP is overexpressed in older cardiac tissue. Thus, the protein and gene can be used as targets to develop drugs to potentially reverse age-related declines in cardiac function. Anti-sense nucleic acids that down regulate translation of p49/STRAP mRNA would be expected to possibly reverse some age-related deterioration in cardiac function. Likewise, agents that bind to and inactivate the p49/STRAP protein would be expected to possibly reverse some age-related deterioration in cardiac function.

Since p49/STRAP binds to and affects the activity of SRF, and can bind to SRF at the same time other cofactors bind to SRF, p49/STRAP is useful in assays measuring the activity of SRF and cofactors for SRF. Those assays can be used to develop other drugs and treatments that target SRF or SRF-related gene expression, and can be used simply to better understand cardiac gene regulation.

SRF and some of the genes shown below to be regulated by p49/STRAP are linked to disease processes, including human T-cell leukemia (43), DNA damage in cortical neurons (44), colon cancer (45), and others (46). Thus, p49/STRAP is useful in investigating these disease processes and possibly in developing treatments for them.

An antibody against p49/STRAP may be used to study the biology of p49/STRAP, including its expression, localization, and interaction with other proteins. The antibody may also be studied for possible clinical utility in decreasing activity levels of p49/STRAP or targeting drugs to tissues where p49/STRAP is expressed.

Recombinant cells with insertions or deletions in the p49/STRAP gene are useful to study the biology of p49/STRAP and the heart, and may be studies for clinical utility in decreasing p49/STRAP activity.

In particular embodiments of the invention, the isolated peptide or protein includes 15 or more, 20 or more, 30 or more, or 50 or more residues at least 90% identical to the fragment of a p49/STRAP protein.

In particular embodiments of the invention, the isolated peptide or protein includes 10 or more, 15 or more, 20 or more, 30 or more, or 50 or more residues identical to the fragment of a p49/STRAP protein.

In particular embodiments, the p49/STRAP protein is SEQ ID NO:1. In other embodiments, it is SEQ ID NO:2.

In particular embodiments, the p49/STRAP protein is a human or a mouse p49/STRAP protein. The human p49/STRAP may be SEQ ID NO:1 or it may be a mutant or a variant. Likewise, the mouse p49/STRAP may be SEQ ID NO:2 or it may be a mutant or a variant.

The p49/STRAP proteins and genes of the invention may be wild-type or variant sequences. The variant sequences may be naturally occurring or engineered. An engineered p49/STRAP protein may include non-natural amino acids or be chemically modified, e.g., by modification of the side chains of some of the amino acids.

Preferably, the p49/STRAP protein is at least 50%, and more preferably at least 60% identical to both SEQ ID NO:1 and SEQ ID NO:2.

Preferably the p49/STRAP protein affects expression of at least some SRF-regulated genes, which can be assayed as described in Example 1.

In particular embodiments, the isolated p49/STRAP protein is at least 60%, at least 70%, at least 80%, or at least 90% identical to SEQ ID NO:1.

In particular embodiments, the isolated p49/STRAP is at least 60%, at least 70%, at least 80%, or at least 90% identical to SEQ ID NO:2.

In particular embodiments, the p49/STRAP protein is a naturally occurring p49/STRAP in a mammal.

In particular embodiments of the invention, the isolated p49/STRAP is a chromosomal gene. In other embodiments, it is a cDNA.

In particular embodiments, the p49/STRAP gene is a human gene, e.g. SEQ ID NO:3. In other embodiments, it is a mouse gene, e.g., SEQ ID NO:4.

In particular embodiments, the p49/STRAP gene encodes a protein that is at least 60%, 70%, 80%, or 90% identical to SEQ ID NO:1. In other embodiments, the p49/STRAP gene encodes a protein that is at least 60%, 70%, 80%, or 90% identical to SEQ ID NO:2.

In particular embodiments, the coding portions of the p49/STRAP gene of an isolated nucleic acid are at least 60%, at least 70%, or at least 80% identical to the coding portions of SEQ ID NO:3.

In particular embodiments, the coding portions of the p49/STRAP gene of an isolated nucleic acid are at least 60%, at least 70%, or at least 80% identical to the coding portions of SEQ ID NO:4.

Particular embodiments of the invention include an isolated nucleic acid containing a fragment of at least 10 nucleotides, at least 15 nucleotides, at least 20 nucleotides, at least 30 nucleotides, at least 50 nucleotides, at least 75 nucleotides, or at least 100 nucleotides of SEQ ID NO:3 or SEQ ID NO:4, or a complement thereof.

Other embodiments of the invention include an isolated nucleic acid containing 20 or more, 30 or more, 50 or more, 75 or more, or 100 or more nucleotides at least 90% identical to a fragment of SEQ ID NO:3 or SEQ ID NO:4, or a complement thereof.

Other embodiments of the invention include an isolated nucleic acid comprising 100 or more nucleotides at least 65%, at least 70%, at least 75%, or at least 80% identical to SEQ ID NO:3 or SEQ ID NO:4, or a complement thereof.

In particular embodiments of the method of identifying a nucleic acid molecule related to a p49/STRAP gene involving hybridizing a fragment of SEQ ID NO:3 or SEQ ID NO:4 to a nucleic acid sample, the nucleic acid sample is a library of nucleic acid molecules carried in a population of a host microorganism. Detecting the presence of the complex can involve detecting a colony or plaque of microorganisms carrying the nucleic acid molecule related to a p49/STRAP gene. The microorganisms can be, for instance, bacteria, yeast, viruses, or phage.

In a particular embodiment of the method, the isolated nucleic acid containing a fragment of at least 10 nucleotides of SEQ ID NO:3 or SEQ ID NO:4, or a complement thereof, is a primer, and the method involves hybridizing a second primer to the nucleic acid sample and amplifying the nucleic acid molecule related to a p49/STRAP gene by PCR.

The recombinant host cells of the invention that contain an isolated nucleic acid molecule of the invention or express a protein or peptide of the invention in particular embodiments are bacteria, fungi, yeast, or mammalian host cells. The mammalian host cells may be in vitro or in vivo in a mammal.

The isolated nucleic acid molecule contained in the recombinant host cells is a recombinant nucleic acid molecule.

The antibodies of the invention that specifically recognize a p49/STRAP gene may be monoclonal or polyclonal. They may be whole antibody molecules or fragments such as Fab'. They may be generated in a vertebrate or selected in vitro by a technique such as phage display. They may also be chemically modified.

One embodiment of the invention is a recombinant cell comprising an insertion in a p49/STRAP gene.

The recombinant cell is typically a mammalian cell where the p49/STRAP gene containing the insertion is located on the chromosome. But the gene containing the insertion can also be episomal in a mammalian cell. The recombinant cell can also be, for instance, a yeast cell. The cell can be in vitro or in vivo.

The insertion in particular embodiments can be in SEQ ID NO:3 or SEQ ID NO:4.

In particular embodiments, the insertion inactivates the gene.

One embodiment of the invention provides an isolated nucleic acid capable of hybridizing to a p49/STRAP gene under hybridization conditions of 6×SSC, 5×Denhardt's, 0.5% SDS, and 100 micrograms/ml fragmented and denatured salmon sperm DNA hybridized overnight at 65° C. and washed two times at room temperature for 10 minutes each in 2×SSC, 0.1% SDS and one time at 55° C. for one hour; wherein the p49/STRAP gene is SEQ ID NO:3 or SEQ ID NO:4. See Sambrook, Joseph, and David W. Russell, *Molecular Cloning: A Laboratory Manual*, third edition, 2001, Cold Spring Harbor Laboratory Press, Cold Spring Harbor, N.Y., for recipe for SSC.

In particular embodiments, the third wash can be more stringent, e.g., at 65° C. for one hour, or with 1×SSC 0.1% SDS, or 0.2×SSC, 0.1% SDS, at 55° C. or 65° C.

One embodiment of the invention provides a method of inhibiting proliferation of cancer cells involving contacting the cancer cells with an effective amount of p49/STRAP protein.

In a particular embodiment, the method involves transforming the cancer cells with a recombinant nucleic acid encoding the p49/STRAP protein and expressing the p49/STRAP protein from the recombinant nucleic acid.

In a particular embodiment, the cancer cells are colon cancer cells. In other embodiments, the cancer cells are non-small cell lung cancer cells, breast cancer cells, glioblastoma cells, melanoma cells, prostate cancer cells, non-hodgkin's lymphoma cells, hodgkin's lymphoma cells, or leukemia cells.

Another embodiment of the invention provides a method of detecting SRF involving contacting a sample suspected of containing SRF with a labeled p49/STRAP or SRF-binding peptide thereof, and detecting the label.

An SRF-binding peptide of p49/STRAP can be identified by synthesizing artificial peptides composed of portions of the p49/STRAP protein sequence (e.g., peptides of 6-30 amino acid residues) and testing the peptides for binding to immobilized SRF. Binding to SRF can be tested, e.g., by immobilizing the peptides, contacting the immobilized peptides with SRF, and then testing for bound SRF by ELISA with antibodies against SRF. Peptides of p49/STRAP can also be generated by digesting the protein with specific proteases such as trypsin, or by expression of peptides by recombinant DNA means.

In some embodiments, the method of detecting SRF further includes removing unbound labeled p49/STRA or SRF-binding peptide thereof before detecting the label.

The label on p49/STRAP or on an SRF-binding peptide thereof can be, e.g., a radioactive isotope, a peroxidase, green fluorescent protein, or a luciferase stably attached to the protein or peptide. Peroxidase, GFP, or luciferase can be attached to p49 or a peptide by expression of a fusion protein by recombinant DNA techniques. A radioactive isotope can be stably attached by methods known in the art. For instance, I-131 can be attached by the IODO-GEN method (Pierce Biotechnology, Inc., Rockford, Ill.) (49).

It has been observed that dispersion of generations and cell cycle variability increases with population doubling level in cultured human diploid cells (50). P49/STRAP may also inhibit cell proliferation and alter cell cycle variability.

The invention will now be illustrated by the following non-limiting examples.

EXAMPLES

Example 1

Cloning of p49/STRAP and Characterization of Its Biological Activity as a Transcription Regulator that Binds to SRF Introduction In an effort to identify potential SRF cofactors that may contribute to cardiac gene regulation during aging, we performed yeast two-hybrid screening using both SRF NH2-terminal and COOH-terminal portions as bait. Here we report the identification of a novel transcription regulator, p49/STRAP, isolated with the SRF COOH-terminal bait, and propose a model of gene regulation by SRF, p49/STRAP, and other cofactors. The protein p49/STRAP displayed functional cooperation with SRF and myocardin, and repressed the ANF promoter activity which was strongly induced by myocardin. The p49/STRAP mRNA was highly expressed in fetal and postnatal hearts, and was increased by approximately 45% in old compared with young adult hearts. The age-specific and cardiac-specific changes of p49/STRAP and other SRF cofactors in senescence may reflect a dynamic pattern of well regulated gene expression during the process of adult aging.

Experimental Procedures

Yeast Two-Hybrid System.

The bait construct containing the NH2-terminus of SRF protein (1-244 residues), and another containing the COOH-terminus of SRF protein (247-499 residues) were each constructed by fusing the SRF fragments to the GAL4 DNA-binding domain in the pGBT9 vector (Clontech). The constructs were then used to screen an EML cDNA library (24) and a human heart cDNA library (Clontech) with a method described by Zhang et al. (24). The cDNA clones representing potential SRF-interacting proteins were sequenced and were compared with the GenBank database by using Blast Search.

Cloning of Full-Length Coding Region Sequence of p49/STRAP.

Two independent cDNA clones (G65, G78), which were isolated with SRF COOH-terminal bait construct, matched a single gene in the GenBank database which has not been previously characterized (we named it p49/STRAP). The full-length coding region of the mouse and human p49/STRAP gene were amplified by PCR using heart cDNA samples (Clontech). The sequences have been submitted to GenBank with the accession numbers AY611629 and AY611630.

Antibodies and Plasmid Constructs.

A polyclonal antibody against a peptide (KSKKGTEDALLKNQRRAQ, SEQ ID NO:5) of the p49/STRAP protein was commercially generated by standard procedures (Genemed Synthesis Inc., CA). The p49/STRAP antibody was shown to be specific for p49/STRAP in whole-cell lysates by Western blotting with competing peptide (figure not shown). Other antibodies that were employed include HA.11 (Covance), Flag (Sigma), and SRF (Santa Cruz).

Expression plasmid constructs pcDNA-HA-p49/STRAP (wild-type), pcDNA3-HA-p49/STRAP (1-91), and pcDNA3-HA-p49/STRAP (1-232) were constructed by fusing the wild-type and mutant p49/STRAP to HA tag in pcDNA3-HA vector. HA stands for hemaglutinin, a short peptide used as a tag recognized by a commercially available antibody. pCMV-Flag-SRF was assembled by fusing the wild-type SRF to Flag tag in pCMV-Tag2 vector (Stratagene). The pGEX4T1-SRF and pGEX4T1-dmSRF were formed by fusing the SRF and dmSRF (a double mutant form of SRF) (25) to GST in pGEX4T1 vector (Amersham). All the DNA constructs were verified with sequencing analysis.

In Vitro Protein Interaction Assays.

GST fusion proteins were purified with glutathione-conjugated agarose beads (Sigma). The p49/STRAP protein was translated in vitro using a TNT Quick Coupled Transcription/Translation System (Promega) and pcDNA3-p49/STRAP plasmid in the presence of [$^{35}$S]-methionine (Amersham Bioscience) according to the manufacturer's instruction. In the in vitro binding assay, 2 µg of agarose-bound GST fusion proteins were incubated with [$^{35}$S]-methionine-labeled p49/STRAP protein for 1 hr at 4° C. in NETN buffer (20 mM Tris.HCl, pH 8.0, 1 mM EDTA, 1% NP-40, 150 mM NaCl, 0.5% glycerol, 1× protease inhibitor mix). Beads were washed four times with NETN buffer and then analyzed on SDS-PAGE gels and binding activity detected by autoradiography.

In Vivo Protein Interaction Assays in Yeast.

Interaction between SRF and p49/STRAP was first tested in vivo in yeast cells using well established techniques. Briefly, a "bait" plasmid containing SRF COOH terminus and the gene for tryptophan synthesis, and a target plasmid containing p49/STRAP cDNA and the gene for leucine synthesis, were co-transformed into the yeast cells. The yeast host strain contains a His reporter gene under transcriptional control of the GAL UAS. Transcription factors such as GAL4 consist of two discrete modular domains: the DNA-binding domain and the activation domain. The "bait" SRF gene was expressed as a fusion to the GAL4 DNA-binding domain (DNA-BD), while the p49/STRAP gene was expressed as a fusion to the GAL4 DNA activation domain (AD). When SRF and p49/STRAP interact, the DNA-BD and AD are brought into proximity, thus activating transcription of the reporter genes tryptophan, leucine, and histidine, and thereby allowing the transformed yeast cells to grow on plates containing tryptophan, leucine, and histidine triple dropout medium.

Northern Blotting and Western Blotting.

Healthy young adult (3-month-old) and old (20-month-old) mice were obtained from colonies maintained by the National Institute on Aging (NIA) under contractual agreement with Harlan Sprague Dawley, Inc. (Harlan, Ind.). The human heart mRNA samples were obtained from Biochain Institute (Hayward, Calif.). The human tissue blot, human cardiovascular system blot, and mouse tissue blot were purchased from Clontech. The Northern blotting and Western blotting were performed as described (6, 25). The studies were conducted with Institutional Review Board approval and in accordance with the NIH Guiding Principles for Research Involving Animals and Human Beings.

Co-Immunoprecipitation.

The expression plasmid constructs containing p49/STRAP, SRF, and either myocardin or Nkx2.5 were cotransfected into NIH3T3 cells by using Lipofectamine (Invitrogen). At 48 hours after the transfection, cells were harvested and the whole-cell lysate was isolated. The lysate proteins were incubated with primary antibody diluted to 1:1000 and bound to protein A/G-Agarose beads for 2 hr at 4° C. in IP buffer (2% glycerol, 1% Nonidet P-40, 1 mM EDTA, 20 mM Tris.HCl, pH 8.0, 100 mM NaCl, 10 mM MgCl$_2$, 0.1 mM ZnSO$_4$, 1× protease inhibitor cocktail [Roche]). Beads were then washed four times with a cold buffer containing 0.5% glycerol, 1% Nonidet P-40, 1 mM EDTA, 20 mM Tris.HCl, pH 8.0, 100 mM NaCl, 10 mM MgCl$_2$, 0.1 mM ZnSO$_4$, and 1× protease inhibitor cocktail, and bound proteins were separated via sodium dodecyl sulfate-10% polyacrylamide (SDS-PAGE) gel and transferred to nitrocellulose membranes (Bio-Rad).

Transfection Assays.

Transient transfections were carried out with the Lipofectamine and Plus reagents (Invitrogen). Approximately 4 hr after the transfection was initiated, cells were placed in DMEM with 10% FCS and incubated overnight. The cells were then cultured in DMEM with 0.1% FCS for another 24 hr, and then placed in DMEM with 20% FCS for an additional 3.5 hr. Firefly luciferase activity was measured as relative light units. To control for variability, the number of relative light units from individual transfection experiments was normalized by measuring Renilla luciferase activity expressed from a cytomegalovirus promoter-driven vector in the same samples. Individual transfection experiments were carried out in triplicate, and the results were reported as mean firefly luciferase/Renilla luciferase activity (mean±S.D.) from representative experiments.

Subcellular Localization.

The expression plasmid (pLP-EGFP-p49/STRAP) containing the Enhanced Green Fluorescent Protein (EGFP)-p49/STRAP fusion protein was generated using the Creator DNA cloning system (Clontech). At approximately 30 hr after the transfection, the expression of EGFP-p49/STRAP fusion protein was examined by fluorescence microscopy using a Zeiss Deconvolution microscope with AxioVison version 3.1 software.

Electrophoretic Mobility-Shift Assays (EMSAs).

EMSAs were performed as described by using the SRE consensus oligonucleotide, which is derived from the c-fos promoter (5'-GGATGTCCATATTAGGACATCT-3', SEQ ID NO:6) (6). The in vitro translated SRF and p49/STRAP, as well as the protein from NIH3T3 cells transfected with pAd-Track-CMV-SRF and pcDNA3-HA-p49/STRAP plasmids, were employed for EMSAs.

Results p49/STRAP is a Novel Protein that Binds to and Modulates SRF.

Sequencing analysis and Blast Search against the GenBank database revealed that two independent yeast cDNA clones, which were isolated with the SRF COOH-terminal bait, matched a single gene in the GenBank database, the function of which remains uncharacterized.

The full-length coding region sequence of this gene was amplified from mouse cardiac cDNA by PCR. This gene encoded a 441-amino acid protein with a predicted mass of 49 kDa; therefore we named it p49/STRAP (SRF-dependent Transcription Regulation Associated Protein). The overlapping sequence of the two cDNA clones covered 133 amino acids of the p49/STRAP protein (FIG. 1), indicating that this domain was important for its binding to the SRF protein. The human p49/STRAP gene was also amplified from human cardiac cDNA. Sequence alignment revealed 66% homology between human (SEQ ID NO:1) and mouse (SEQ ID NO:2) p49/STRAP (FIG. 1). The mouse (SEQ ID NO:4) and human (SEQ ID NO:3) p49/STRAP cDNAs were found to be 73.5% identical (data not shown).

To determine whether p49/STRAP possesses conserved protein domains or motifs, the p49/STRAP sequence was compared with the NCBI Conserved Domain database, Pfam Protein Family database, and SWISS-PRO Protein database. However, no existing domain or motif matched the p49/STRAP gene, indicating that p49/STRAP may belong to a new class of as yet uncharacterized proteins.

p49/STRAP is Expressed in the Heart and Other Tissues.

Northern blotting revealed that three p49 isoforms were detected in mouse tissues. Among the tissues tested, mouse heart, liver, kidney and testes had a high level of p49 expression (FIG. 2A).

Figure 2B:
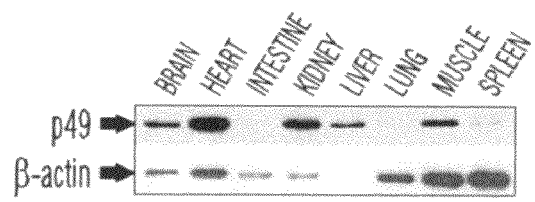

Western blotting using mouse tissue lysates demonstrated that the p49/STRAP antibody recognized a 49 kDa protein (FIG. 2B). This antibody-protein binding could be blocked by the p49/STRAP peptide (figure not shown), indicating that the 49 kD protein is the main protein product of this gene.

Figure 2C:
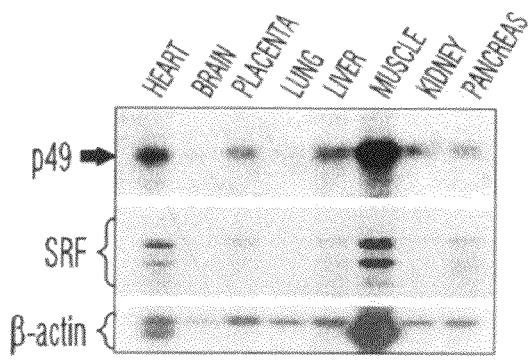
Figure 2D:
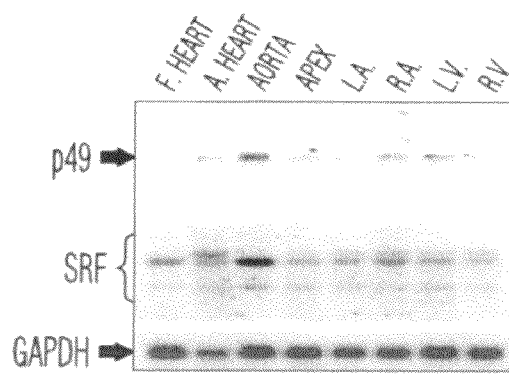

Among human tissues, human heart and skeletal muscle had the highest levels of p49/STRAP mRNA, while the brain and lungs had the lowest levels of p49/STRAP mRNA (FIG. 2C). Unlike the mouse tissue, human tissue had only one major p49/STRAP transcript, at approximately 2.2 kb. In the human cardiovascular system, the p49 mRNA level is higher in the adult than in the fetal heart (FIG. 2D).

p49/STRAP is Increased in Expression in the Aging Heart and in the Heart of Cardiomyopathy.

Figure 3A:
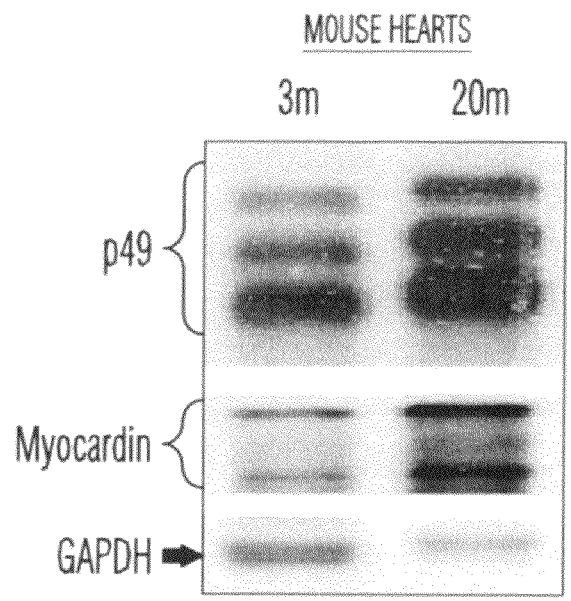
FIGS. 3A-D. 3A: Both p49/STRAP and myocardin mRNA levels are increased in the hearts of old (20 month-old) compared to young adult (3-month old) mice. 3B: Protein expression levels in mouse hearts (three 3-month-old and three 20-month-old mice). The panel shows p49 levels are increased in the older mice. 3C: mRNA levels of p49 in human heart. This panel shows both p49 and myocardin mRNA levels are increased in the older heart. 3D: p49/STRAP mRNA level is increased 4-fold in SRF transgenic (Tg) compared with non-transgenic (NTg) mice.
Figure 3B:
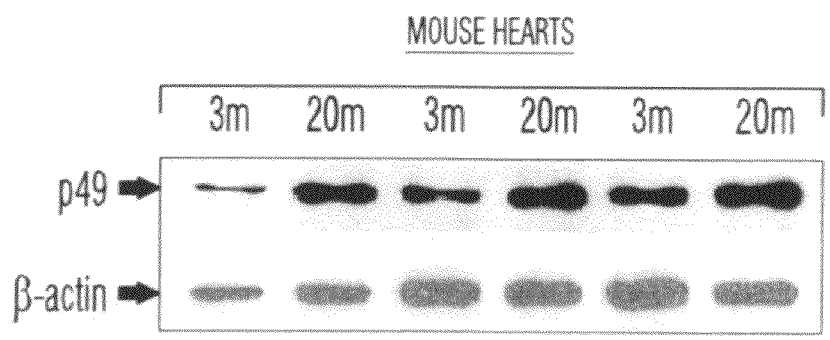
Figure 3C:
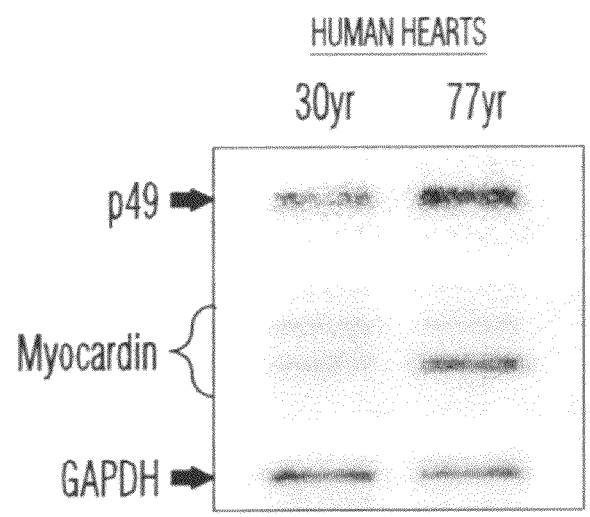

To determine whether there might be an age-related change of p49/STRAP expression in the heart, the expression of p49/STRAP was determined in the myocardium of young-adult and old mice. Western blotting analysis revealed that the cardiac p49/STRAP protein level in 20-month-old mice was approximately 45% higher than in 3-month-old mice (FIG. 3B). The p49/STRAP mRNA was also increased in the heart of the 20-month-old compared with 3-month-old mice (FIG. 3A). In humans, the age-related change was also observed, as shown in FIG. 3C, p49/STRAP mRNA was increased in a 77-year-old individual compared with a 30-year-old individual.

Figure 3D:
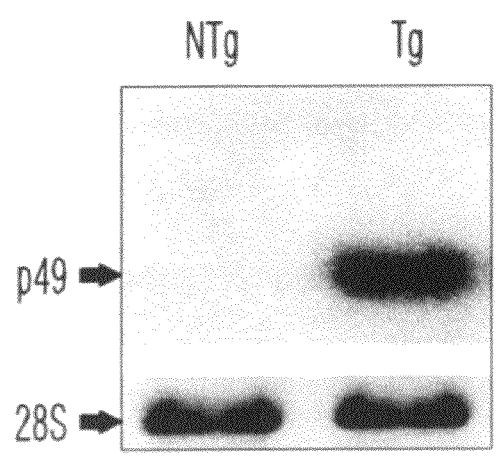

To test whether the expression of p49/STRAP might be associated with a pathological condition, the level of p49/STRAP expression was examined in the myocardium of SRF transgenic mice that suffered from cardiomyopathy (6). Northern blotting revealed a 4-fold increase of p49/STRAP in the heart of adult transgenic compared to that of wild-type mice (FIG. 3D), suggesting overexpression of p49/STRAP is linked to cardiomyopathy.

p49/STRAP Interacts with SRF In Vitro and In Vivo.

To confirm the physical interaction between p49/STRAP and SRF proteins, we first transformed both the SRF bait plasmid containing SRF COOH-terminus and the yeast plasmids containing p49/STRAP protein back into yeast cells. The transformants grew on the —Trp/-Leu/-His triple dropout plates, indicating that the two proteins interact in the yeast cells.

Figure 4A:
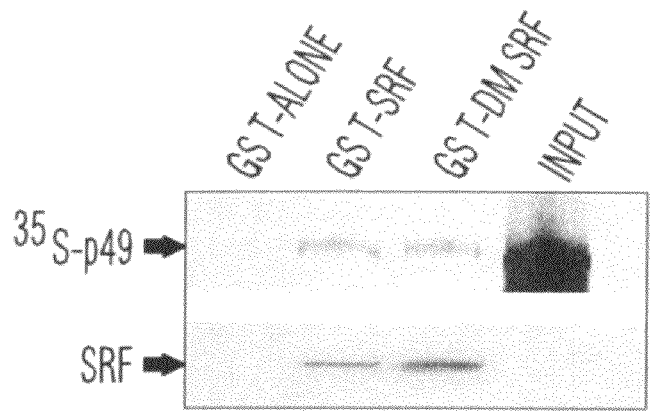
FIGS. 4A-D. Autoradiogram showing $^{35}$S-p49 levels and western blots showing the levels of other proteins in GST pull-down assays (4A) and co-immunoprecipitation assays (4B-D), as described in Example 1.

Then we tested whether p49/STRAP binds to SRF in vitro. SRF-glutathione-S-transferase (GST) fusion proteins were prepared and bound to agarose-glutathione beads. $^{35}$S-labelled p49/STRAP was synthesized by in vitro translation and mixed with the beads coated with GST, GST-SRF, or GST-dmSRF. After binding and washing of unbound proteins, the bound proteins were removed by boiling in SDS and analyzed by SDS-PAGE. As shown in FIG. 4A, $^{35}$S-labeled in vitro translated p49/STRAP protein bound to both immobilized GST-SRF (wild-type) and GST-dmSRF (a double mutant form of SRF) (25), but not to GST protein alone, indicating that p49/STRAP interacts with both the wild-type form and the mutant form of SRF proteins, and that point mutations within the DNA binding domain of SRF did not affect the interaction between SRF and p49/STRAP. The lower panel in FIG. 4A is a western blot with anti-SRF antibody. This panel shows the protein eluted from the beads also contained SRF, indicating that p49 bound to SRF.

Figure 4B:
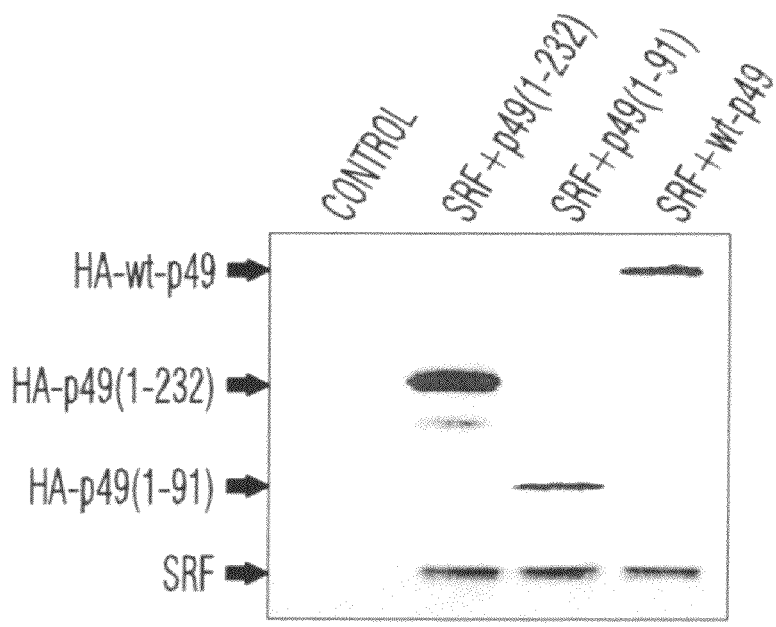

To test whether the interaction between p49/STRAP and SRF could occur in vivo within mammalian cells, we transfected NIH3T3 cells with plasmid constructs containing wild-type and two mutants of p49/STRAP tagged with HA epitope, and a plasmid construct containing Flag-SRF. The results are shown in FIG. 4B. The control cells expressed no foreign protein. The cells of the other three lanes expressed SRF and the HA-labeled form of p49 listed at the top of the gel lanes. In the top portion of FIG. 4B, cell extracts were prepared and immunoprecipitated with anti-SRF antibody. The immunoprecipitate was then western blotted with anti-HA antibody, which binds to the HA-p49. The results show that all three forms of p49—p49(1-232), p49(1-91), and wtp49—were immunoprecipitated with anti-SRF, showing they bound to SRF. In the lower panel, the extracts were immunoprecipitated with anti-HA, and western blotted with anti-SRF. This panel of FIG. 4B shows also that SRF bound to all three forms of p49 in vivo.

Analysis of the previously isolated two yeast cDNA clones that interacted with the SRF bait plasmid suggested that a domain from residue 53 to residue 185 in the p49/STRAP protein is important for its interaction with the SRF protein, since that region of overlap was found in both of the two isolated cDNA clones. However, the in vivo p49/STRAP-SRF interaction data indicated that the protein fragment from residue 1 to 91 in the p49/STRAP protein is sufficient for interaction with SRF.

SRF Simultaneously Binds to p49/STRAP and Other Cofactors.

Figure 4C:
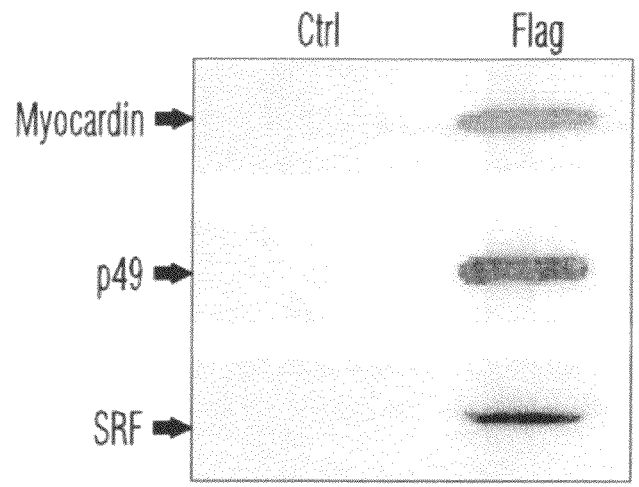
Figure 4D:
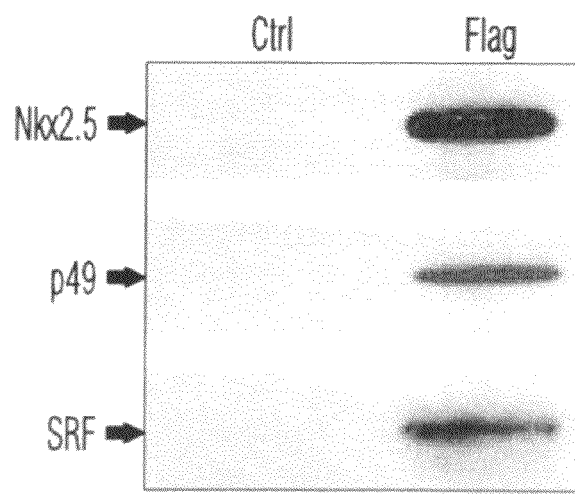

Since p49/STRAP binds mainly to the COOH-terminus of SRF, we hypothesized that other SRF cofactor(s) that interact with the NH2-terminus of the SRF protein could potentially also bind to SRF at the same time. To test this hypothesis, we performed a parallel transfection assay. One set of cells was transfected with p49/STRAP, myocardin, and Flag-SRF expression plasmids (FIG. 4C); the other set of cells was transfected with p49/STRAP, Nkx2.5, and Flag-SRF expression plasmids (FIG. 4D). Control cells carried no plasmids. The cell extracts were immunoprecipitated with anti-Flag, and the immunoprecipitate was western blotted with anti-myocardin, anti-Flag (binding Flag-p49), or anti-SRF antibodies. As shown in FIGS. 4C and 4D, a three-protein complex was precipitated in each case, indicating that SRF could simultaneously interact with both p49/STRAP and another cofactor, either myocardin or Nkx2.5.

p49/STRAP is a Nuclear Protein that does not Bind to SRE.

SRF is a nuclear protein with three nuclear localization signal sequences in its coding region (27). To identify whether p49/STRAP also localizes to the nucleus, an expression plasmid containing EGFP-p49/STRAP fusion protein was transfected into NIH3T3 cells. Fluorescence microscopy showed the fusion protein was localized within the nucleus (data not shown). Since p49 was isolated based on its ability to interact with SRF COOH-terminus which contains SRF transcription activation domain, it was not expected that p49/STRAP would form a ternary complex with SRF at the site of the SRF-response element (SRE). EMSAs using proteins from both cell lysate and in vitro translated p49/STRAP and SRF revealed that no additional band was shifted by anti-SRF or anti-HA antibodies (data not shown) in the presence of DNA fragment corresponding to c-fos promoter that contains SRE, thus confirming that p49/STRAP did not form the ternary complex with SRF at the site of SRE.

p49/STRAP Modulates the Transcriptional Activation of Cardiac Genes.

Figure 5A:
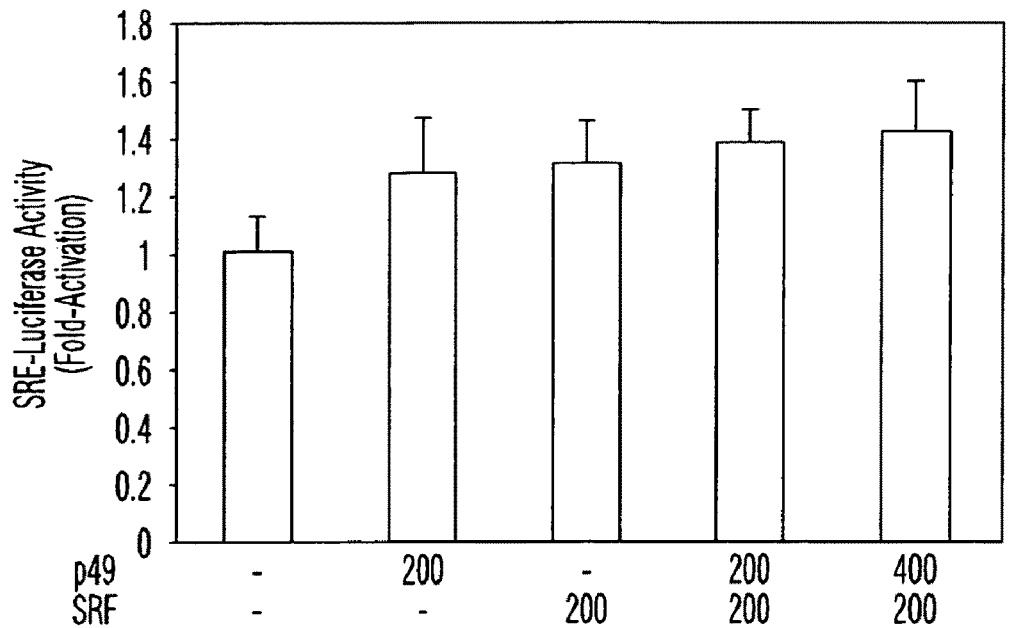
FIGS. 5A-D. 5A: Bar graph showing the effect of p49 and SRF expression on the SRE-luciferase activity. 5B: Bar graph showing the regulation of cardiac actin promoter activity by p49 and SRF expression. 5C: Bar graph showing regulation of MLC2v promoter activity by p49 and SRF. 5D: Bar graph showing p49 represses the myocardin-induced ANF promoter activity.
Figure 5B:
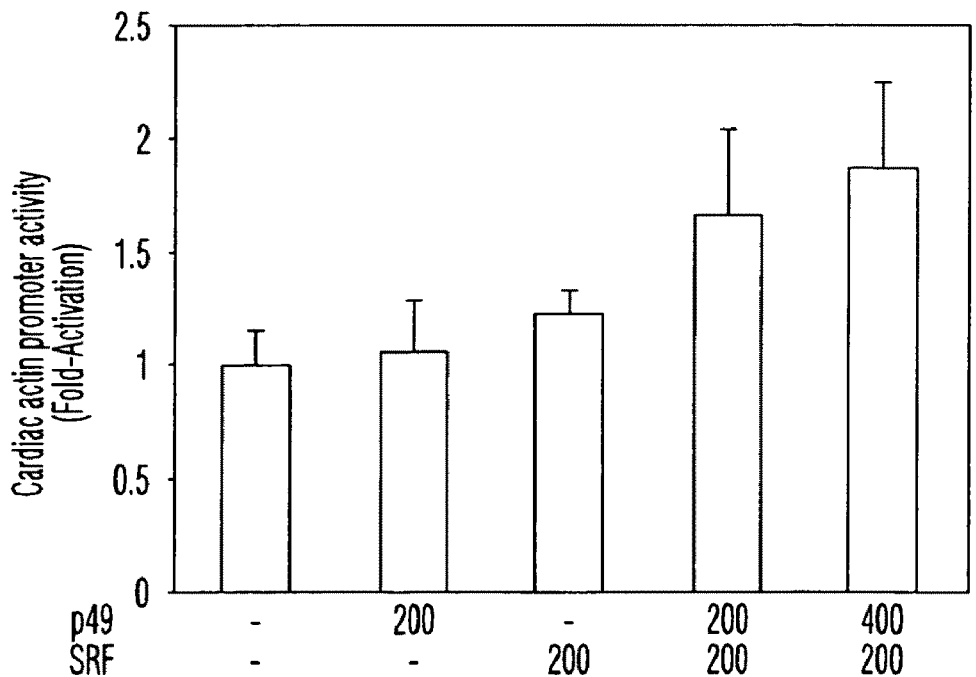
Figure 5C:
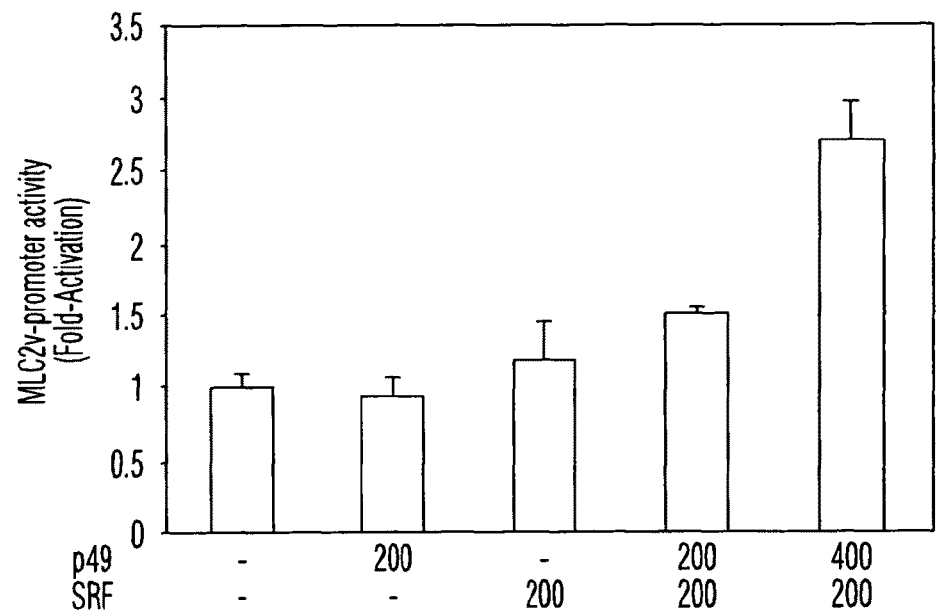
Figure 5D:
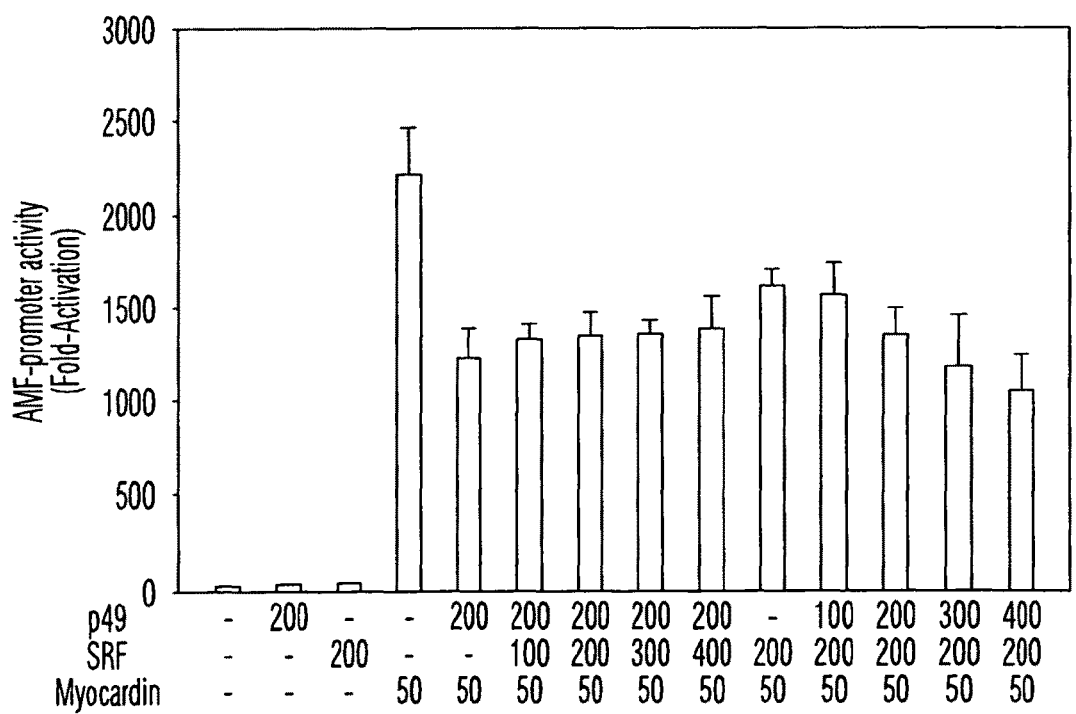

To explore the biological effect of p49/STRAP and the consequences of an elevation of p49/STRAP expression on cardiac gene expression, the promoter activities of c-fos SRE, myosin light chain 2v (MLC2v), cardiac actin, and atrium natriuretic factor (ANF) were utilized as indicators in cell transfection assays. As shown in FIGS. 5A, 5B, and 5C, p49/STRAP activated SRE-luciferase, MLC2v and cardiac actin promoter activity respectively, mainly in cooperation with SRF. However, p49 apparently effectively repressed ANF promoter activity which was strongly induced by myocardin (FIG. 5D).

Discussion

In the present study, we report the identification and characterization of a new gene, p49/STRAP, as a novel SRF-dependent transcription regulator. This gene was initially isolated from yeast two-hybrid screening based on its ability to bind to the SRF COOH-terminus. The subsequent protein-protein binding assays further confirmed that p49/STRAP is an SRF binding protein. In addition, we observed that p49/STRAP could form a protein complex with SRF and also with other SRF cofactor(s), such as myocardin or Nkx2.5. The interaction of p49/STRAP with SRF alone or with both SRF and other cofactors can clearly affect the activation of cardiac gene promoters in diverse ways. Both the p49/STRAP mRNA and protein are highly expressed in the mouse and human heart, and their expression levels increase with advancing age, indicating that p49/STRAP may play a significant role in the regulation of cardiac genes during adult aging.

The sequence of the p49/STRAP protein is conserved between human and mouse. However, to date the p49/STRAP protein sequence does not match any known conserved protein domain or known motif that has been deposited in several public databases, including the NCBI conserved domain database and Pfam Protein Family database. This suggests that p49/STRAP may belong to a new class of proteins which are yet to be determined. Inasmuch as the p49/STRAP protein does not bind to DNA and does not form a protein complex with SRF at the SRE site, it is likely that p49/STRAP modulates SRF function primarily through its interactions with SRF in the SRF transcriptional activation domain.

SRF target genes are regulated in a complex manner that is partly due to the participation of multiple SRF binding proteins in the co-regulation of SRF target genes. SRF binding proteins include the TCF family proteins (26-30) and other transcription factors/regulators. With the increasing number of SRF cofactors being identified, one emerging question is how SRF cofactors might be recruited by SRF for the SRF-dependent transcriptional regulation. Molecular dissection of the functional domain of SRF has revealed that SRF has two major parts. The NH2-terminus has the DNA-binding domain and the dimerization domain, while the COOH-terminus has the transcriptional activation domain (31, 32). Each part constitutes approximately half of the protein. Most of the SRF cofactors (except ATF6) that have been identified apparently predominantly bind to the SRF NH2-terminus (18, 33, 34). However, we and others have observed that a mutant form of SRF, which substitutes amino acids in the DNA binding domain and thus prevents the proteins from binding to DNA, can still significantly affect the expression of SRF target genes, suggesting that the SRF transcriptional activation domain plays a critical role in the regulation of SRF target genes (25).

Figure 6:
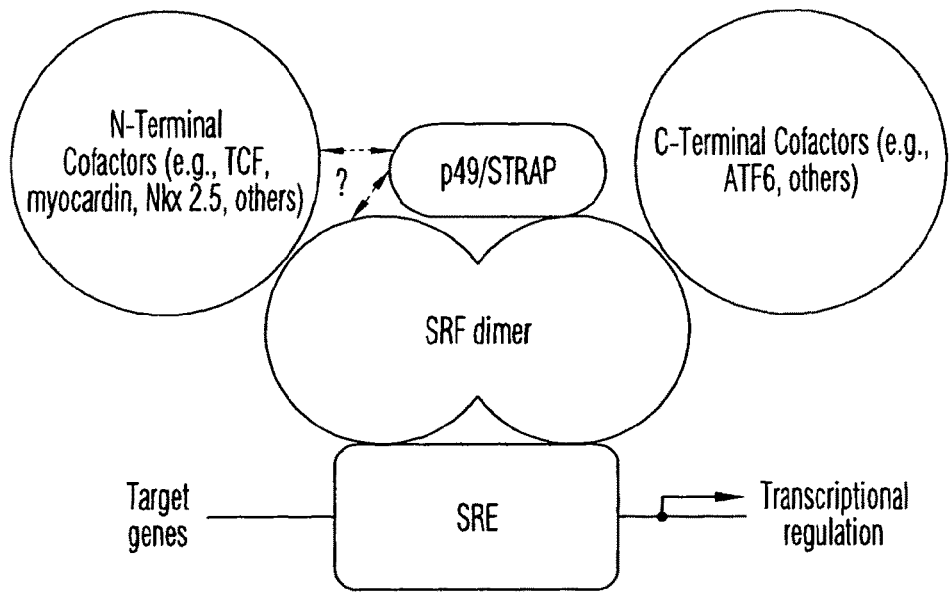
FIG. 6. Schema of a model of the regulation of SRF target genes by SRF, p49, and other cofactors. Two or more cofactors may simultaneously participate in the regulation.

Our finding of the co-immunoprecipitation of two protein complexes containing three proteins, "p49/STRAP-SRF-myocardin" and "p49/STRAP-SRF-Nkx2.5", indicates that p49/STRAP is able to interact with SRF in the presence of another cofactor while they are both bound to SRF. It is likely that multiple cofactors may interact with SRF at any given time within a cell, as shown in FIG. 6. On the NH2-terminus of SRF, many cofactors may competitively bind to SRF, including the TCF family proteins Elk1, SAP-1, and SAP-2 (22, 28); the SAP family protein myocardin (18); the GATA family protein GATA4 (16); Nkx2.5 (35); and Hop (36). On the COOH-terminus of the SRF protein, p49/STRAP and ATF6 may also modulate each other's binding to SRF (37). The concept of multiprotein functional complexes and regulation of intracellular and intercellular processes has been evolving (38, 39). The participation by multiple cofactors and the exchange of the cofactors for each other at any given time may potentially account for the complex patterns of SRF target gene expression in different tissues, at different developmental stages, and under different stress conditions (40). The dynamic interactions among SRF, p49/STRAP and other cofactors may help to determine whether and how much SRF activates or represses its target gene(s).

It has been documented that the RNAs of certain SRF cofactors, such as TCF family proteins (Elk-1, SAP-1 and SAP-2), are present at similar relative levels in many different tissues, suggesting that TCF proteins may serve as universal instead of tissue-specific cofactors (21-23, 33). However, some other cofactors, including myocardin and Nkx2.5, are highly expressed in the heart, and therefore may serve as tissue-specific cofactors. It is plausible that the recently identified Hop protein, which also modulates SRF activity, may also have a similar role (21, 36). In addition, SRF and myocardin have been reported to be well-expressed in the heart during embryogenesis and postnatal development (18, 19, 35). These data indicate that p49/STRAP, SRF and myocardin are well-expressed in the heart during different developmental stages, and suggest that p49/STRAP may also contribute significantly to cardiac gene expression.

We have observed that the cardiac expression of p49/STRAP and myocardin are both increased during adult aging. We previously reported that SRF expression was increased by approximately 20% in the heart of the senescent compared to young adult rodents (5, 7). In contrast, some other transcription factors which are SRF cofactors, including Nkx2.5 and GATA4, have been reported to be decreased during adult aging (41). The age-specific and cardiac-specific increase of some SRF cofactors and decrease of other cofactors are unlikely to be a coincidence, and rather reflect the dynamic pattern of precisely regulated gene expression during the process of adult aging. Recent studies using sophisticated molecular methods have revealed dynamic patterns of gene expression during aging in animals across species, and support the concept that the change in gene expression during adult aging is likely due to "selective gene regulation" rather than random passive decline (42).

Example 2 p49/STRAP Causes Cell Cycle Arrest and Inhibits Tumor Cell Proliferation

Methods.

Cell culture. HT29 cells were grown in DMEM with 10% bovine calf serum at 37° C. in a 5% $CO_2$ atmosphere. To harvest cells or divide for subculture, cells were detached by incubation in trypsin-EDTA solution (Gibco) for approximately 5 minutes at 37° C., then mixed with growth medium to stop the trypsin digestion, centrifuged, and resuspended in growth medium or phosphate-buffered saline (PBS).

Adenovirus vector creation, expression, and culture. The cDNA fragment of the coding region of wild-type p49/STRAP was ligated into the vector pAdTrack-CMV (a gift of Dr. B. Vogelstein at Johns Hopkins Oncology Center, Baltimore, Md.; reference 47) to form a new plasmid "pAdTrack-CMV-p49/STRAP," which was then transformed into a competent bacterial strain E. coli BJ5183 along with a helper plasmid pAdEasy-1 (Stratagene, La Jolla, Calif.). The homologous recombination occurred in the BJ5183 cells, and the p49/Strap recombinant plasmid was then selected based upon kanamycin resistance. The p49/STRAP recombinant plasmid was confirmed by restriction enzyme digestion and DNA sequencing.

Figure 7:
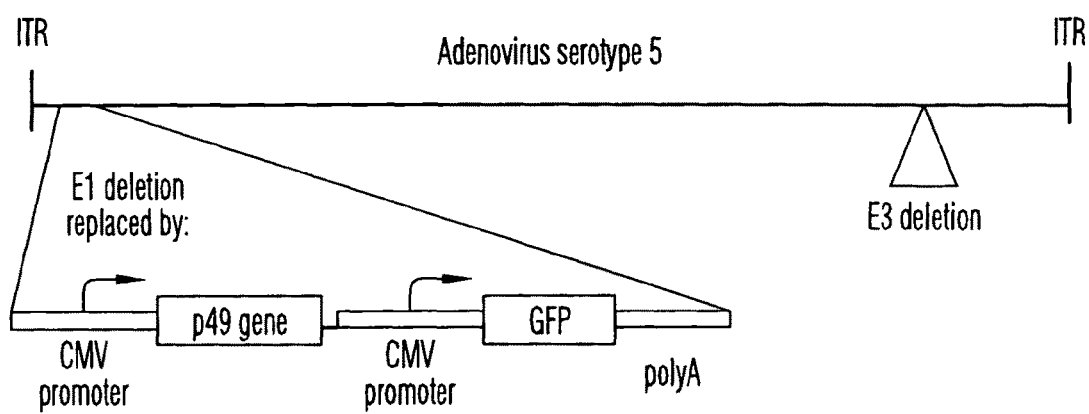
FIG. 7 is a map of the adenovirus vector expressing p49/STRAP.

To produce the recombinant p49/STRAP adenovirus, the p49/Strap recombinant plasmid was transfected into HEK-293 cells, an adenovirus packaging cell line (E1-transformed human embryonic kidney cells). Six days after transfection, the cells were harvested, and the first preparation of recombinant p49/Strap adenovirus was extracted from cells by breaking up the cells through a few cycles of freeze/thaw/vortex. A map of the recombinant p49/STRAP adenovirus is shown in FIG. 7.

To obtain the high titer viral stocks, the p49/STRAP adenovirus supernatant was used to infect 20 flasks of HEK-293 cells. At 48 hours after infection, the cells were harvested and the recombinant adenovirus was extracted from the cells. The adenovirus supernatant was then purified by using CsCl gradient ultracentrifugation. The CsCl was later removed by passing the purified virus through prepacked PD-10 columns (Amersham Biosciences).

MTT assay. Cell proliferation was measured using at MTT cell proliferation kit (Roche Applied Sciences). The assay is based on reduction of a tetrazolium dye by NADH in metabolically active cells. Readings are proportional to the number of metabolically active cells.

Colony formation assay. HT29 cells were harvested and counted. 600 cells were plated in each 60 mm petri dish and incubated at 37° C. overnight. Recombinant adenovirus was then added to the plates the next morning (day 2) at a multiplicity of infection of 10. On day 8, the total number of colonies in each dish were counted, "colony" being defined as an individual cluster of approximately 50 or more cells.

Cell cycle assay. To determine the proportion of cells in the $G_1$, S, and $G_2$+M phases of the cell cycle, cells were harvested by trypsinization. Approximately $10^6$ cells were washed by centrifugation at 1500 rpm in cold PBS, and resuspended in 1 ml cold PBS. The cells were then added drop-wise while vortexing to 1 ml cold 80% ethanol. This was incubated a minimum of 30 min on ice. Cells were pelleted by centrifugation, washed once in PBS, and resuspended in 0.32 ml cold PBS. Propidium iodide was added from a 10 mg/ml stock solution to a final 50 µg/ml and RNAse A was added from a stock solution to a final 50 µg/ml. The solution was vortexed and incubated at 37° C. for 30 minutes in the dark. The cells were placed on ice and analyzed within 1 hour.

Propidium iodide is a dye that binds to DNA. Thus, the amount of dye bound is proportional to DNA content. The cells were analyzed by flow cytometry to determine the relative proportion of cells with a DNA ploidy index of 1 ($G_1$ phase), 2 ($G_2$ and M phases), or a value between 1 and 2 (S phase). The flow cytometry and analysis was conducted as described in reference 48.

Results.

p49/STRAP inhibits proliferation of HT29 tumor cells. HT29 cells, a human colon cancer cell line, were cultured and infected with adenovirus expressing green fluorescent protein (GFP) as a control, or adenovirus expressing p49/STRAP, at a multiplicity of infection (MOI) of 5, 10, 20, or 30. Control uninfected cells were also cultured. The wells of a 96-well plate were seeded with 6,000 cells per well. A starting "time zero" MTT reading of wells containing the control uninfected cells was obtained. Other wells were then infected with adenovirus expressing GFP or p49, or left uninfected. The cells were incubated for 48 hours at 37° C. with the virus. MTT readings were obtained for wells of the 3 groups of cells (GFP infected, p49 infected, or uninfected) after the 48 hours. The time zero reading was subtracted from the 48 hour readings. The value for the uninfected cells was set at 1, and the value for the Ad-GFP and Ad-p49 cells was divided by the value for the uninfected cells to obtain an inhibition ratio. The results are plotted in FIG. 8. The vector expressing p49 inhibited proliferation and gave greater inhibition at the higher multiplicities of infection.

Figure 8:
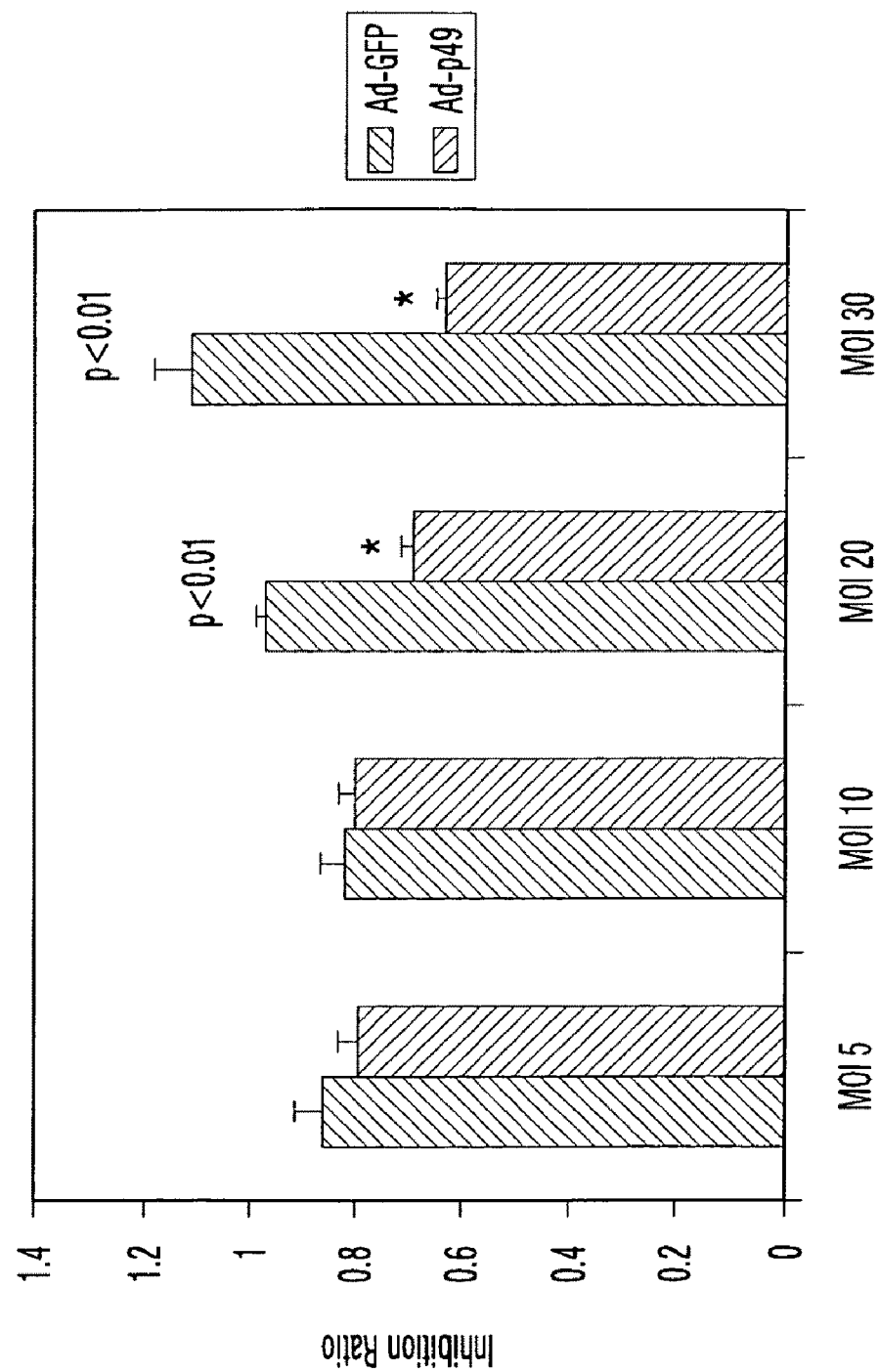
FIG. 8 is a bar graph showing inhibition of HT29 tumor cell proliferation by adenovirus expressing p49/STRAP.
Figure 9:
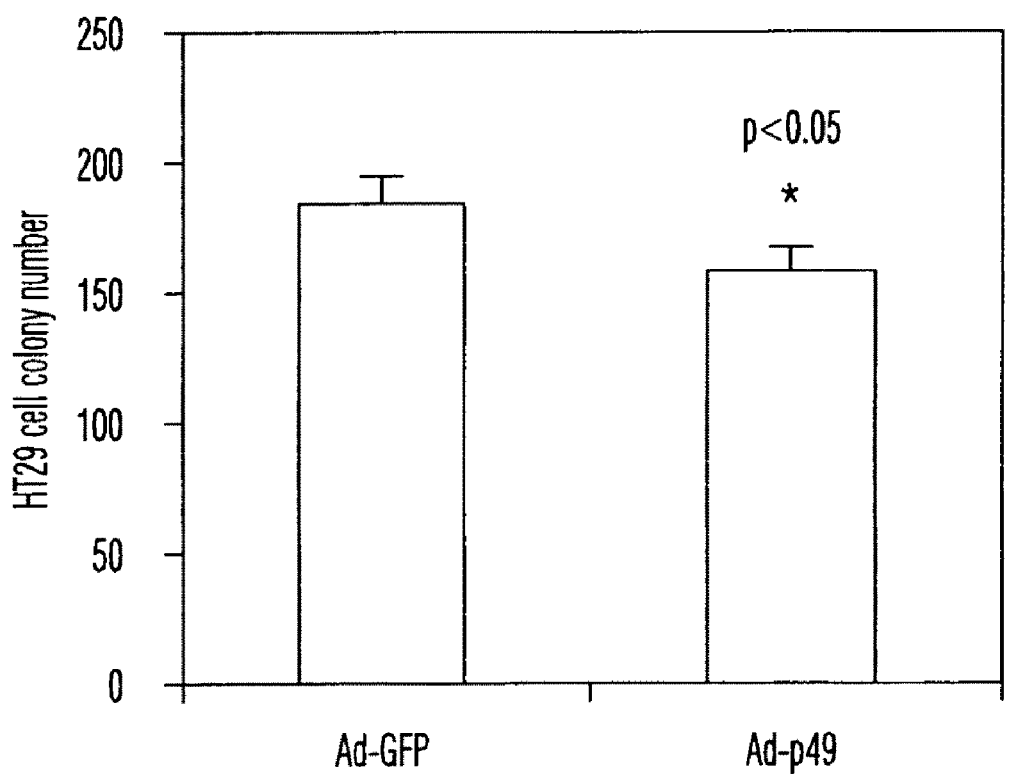
FIG. 9. is a bar graph showing inhibition of HT29 colony formation by infection with adenovirus expressing p49/STRAP.

Colony formation assay. Cultures of HT29 were infected with Ad-GFP or Ad-p49 as described in materials and methods, incubated for 6 additional days, and then the number of colonies was determined. The results are shown in FIG. 8. The experiment was performed in 4 plates in each condition. The results showed that cells infected with the vector expressing p49/STRAP produced a smaller number of colonies than cells infected with the vector expressing GFP, with the difference being statistically significant.

Cell cycle assay. Cells were plated in 60 mm petri dishes at $1 \times 10^6$ cells per plate in culture medium. After 24 hours, Adenovirus expressing GFP or p49/STRAP was added at a multiplicity of infection of 20, 25, or 30. The plates were incubated for another 24 hours at 37° C. Then the cells were harvested and their phase of the cell cycle was determined as described in materials and methods. The results are shown in Table 1 below.

TABLE 1 p49/STRAP inhibits HT29 tumor cells.

| Dose of Adenovirus | Total S-phase no virus (control) | Total S-phase Ad-GFP (control) | Total S-phase Ad-p49 |
|---|---|---|---|
| 20 MOI | 4.70% | 0% | 36.37% |
|  |  | 0% | 23.08% |
| 25 MOI | 0% | 0% | 59.62% |
|  |  | 0% | 68.49% |
| 30 MOI | 4.75% | 12.83% | 92.58% |
|  |  | 0% | 96.16% |

CONCLUSIONS

Expression of p49/STRAP in HT29 tumor cells causes inhibition of cell proliferation and cell cycle arrest in the S phase of the cell cycle in a dose-dependent manner.

CITED REFERENCES

1. Wei J Y. (1992) *N Eng J Med* 327(24), 1735-9.
2. Vaitkevicius P V, Lane M, Spurgeon H, Ingram D K, Roth G S, Egan J J, Vasan S, Wagle D R, Ulrich P, Brines M, Wuerth J P, Cerami A, Lakatta E G (2001) *Proc Natl Acad Sci USA* 98(3), 1171-5.
3. Pugh, K. G. & Wei, J. Y. (2001) *Drugs Aging* 18, 263-76.
4. Tsou, H., Azhar, G., Lu, X. G., Kovacs, S., Peacocke, M. & Wei, J. Y. (1996) *Exp Cell Res* 229, 432-7.
5. Lu, X. G., Azhar, G., Liu, L., Tsou, H. & Wei, J. Y. (1998) *J Gerontol A Biol Sci Med Sci* 53, B3-10.

6. Zhang, X., Azhar, G., Chai, J., Sheridan, P., Nagano, K., Brown, T., Yang, J., Khrapko, K., Borras, A. M., Lawitts, J., Misra, R. P. & Wei, J. Y. (2001) *Am J Physiol Heart Circ Physiol* 280, H1782-92.
7. Zhang, X., Azhar, G., Furr, M. C., Zhong, Y. & Wei, J. Y. (2003) *Am J Physiol Regul Integr Comp Physiol* 285, R552-60.
8. Treisman, R. (1992) *Trends Biochem Sci* 17, 423-6.
9. Shioi T, Kang P M, Douglas P S, Hampe J, Yballe C M, Lawitts J, Cantley L C, Izumo S. (2000) *EMBO J* 19(11), 2537-48.
10. Poser S, Impey S, Trinh K, Xia Z, Storm D R. (2000) *EMBO J.* 19(18), 4955-66.
11. Schratt G, Philippar U, Hockemeyer D, Schwarz H, Alberti S, Nordheim A. (2004) *EMBO J.* 23(8), 1834-44.
12. Belaguli, N. S., Sepulveda, J. L., Nigam, V., Charron, F., Nemer, M. & Schwartz, R. J. (2000) *Mol Cell Biol* 20, 7550-8.
13. Argentin, S., Ardati, A., Tremblay, S., Lihrmann, I., Robitaille, L., Drouin, J. & Nemer, M. (1994) *Mol Cell Biol* 14, 777-90.
14. Miano, J. M. (2003) *J Mol Cell Cardiol* 35, 577-93.
15. Morin, S., Paradis, P., Aries, A. & Nemer, M. (2001) *Mol Cell Biol* 21, 1036-44.
16. Muller, J. G., Thompson, J. T., Edmonson, A. M., Rackley, M. S., Kasahara, H., Izumo, S., McQuinn, T. C., Menick, D. R. & O'Brien, T. X. (2002) *J Mol Cell Cardiol* 34, 807-21.
17. Groisman, R., Masutani, H., Leibovitch, M. P., Robin, P., Soudant, I., Trouche, D. & Harel-Bellan, A. (1996) *J Biol Chem* 271, 5258-64.
18. Wang, D., Chang, P. S., Wang, Z., Sutherland, L., Richardson, J. A., Small, E., Krieg, P. A. & Olson, E. N. (2001) *Cell* 105, 851-62.
19. Du, K. L., Ip, H. S., Li, J., Chen, M., Dandre, F., Yu, W., Lu, M. M., Owens, G. K. & Parmacek, M. S. (2003) *Mol Cell Biol* 23, 2425-37.
20. Chen, F., Kook, H., Milewski, R., Gitler, A. D., Lu, M. M., Li, J., Nazarian, R., Schnepp, R., Jen, K., Biben, C., Runke, G., Mackay, J. P., Novotny, J., Schwartz, R. J., Harvey, R. P., Mullins, M. C. & Epstein, J. A. (2002) *Cell* 110, 713-23.
21. Shin C H, Liu Z P, Passier R, Zhang C L, Wang D Z, Harris T M, Yamagishi H, Richardson J A, Childs, G, Olson E N. (2002) *Cell* 11(6): 725-35.
22. Wang Z, Wang D Z, Hockemeyer D, McAnally J, Nordheim A, Olson E N. (2004) *Nature.* 11; 428 (6979): 185-9.
23. Pilz R B, Casteel D E. (2003) *Circ Res.* 28; 93(11): 1034-46.
24. Zhang, P., Behre, G., Pan, J., Iwama, A., Wara-Aswapati, N., Radomska, H. S., Auron, P. E., Tenen, D. G. & Sun, Z. (1999) *Proc Natl Acad Sci USA* 96, 8705-10.
25. Zhang, X., Chai, J., Azhar, G., Sheridan, P., Borras, A. M., Furr, M. C., Khrapko, K., Lawitts, J., Misra, R. P. & Wei, J. Y. (2001) *J Biol Chem* 276, 40033-40.
26. Johansen, F. E. & Prywes, R. (1994) *Mol Cell Biol* 14, 5920-8.
27. Gauthier-Rouviere, C., Vandromme, M., Lautredou, N., Cai, Q. Q., Girard, F., Fernandez, A. & Lamb, N. (1995) *Mol Cell Biol* 15, 433-44.
28. Price, M. A., Rogers, A. E. & Treisman, R. (1995) *Embo J* 14, 2589-601.
29. Gineitis, D. & Treisman, R. (2001) *J Biol Chem* 276, 24531-9.
30. Maira, S. M., Wurtz, J. M. & Wasylyk, B. (1996) *Embo J* 15, 5849-65.
31. Johansen, F. E. & Prywes, R. (1993) *Mol Cell Biol* 13, 4640-7.
32. Norman, C., Runswick, M., Pollock, R. & Treisman, R. (1988) *Cell* 55, 989-1003.
33. Treisman, R. (1994) *Curr Opin Genet Dev* 4, 96-101.
34. Zhu, C., Johansen, F. E. & Prywes, R. (1997) *Mol Cell Biol* 17, 4957-66.
35. Sepulveda, J. L., Vlahopoulos, S., Iyer, D., Belaguli, N. & Schwartz, R. J. (2002) *J Biol Chem* 277, 25775-82.
36. Kook H. Lepore J J, Gitler A D, Lu M M, Wing-Man Yung W, Mackay J, Ferrari V, Gruber P, Epstein J A. (2003) *J Clin Invest* 112(6):863-71.
37. Thuerauf D J, Arnold N D, Zechner D, Hanford D S, DeMartin K M, McDonough P M, Prywes R, Glembotski C C. (1998) *J Biol Chem* 273(32):20636-43.
38. Pardee A B, Reddy G P. (2003) *Gene* 321, 17-23.
39. Kumar V, Carlson J E, Ohgi K A, Edwards T A, Rose D W, Escalante C R, Rosenfeld M G, Aggarwal A K. (2002) *Mol Cell* 10(4), 857-69.
40. Li X, Rosenfeld M G. (2004) *Nature* 427(6976), 687-8.
41. Bodyak, N., Kang, P. M., Hiromura, M., Sulijoadikusumo, I., Horikoshi, N., Khrapko, K. & Usheva, A. (2002) *Nucleic Acids Res* 30, 3788-94.
42. Helfand, S. L. & Inouye, S. K. (2002) *Nat Rev Genet* 3, 149-53.
43. Wycuff, D. R., Yanites, H. L., & Marriott, S. J. (2004) *Virology* 324, 540-53.
44. Chang, S. H., Poser, S, & Xia, Z. (2004) *Neurosci.* 24, 2277-85.
45. Patten, L. C., Belaguli, N. S., Baek, M. J, Fagan, S. P., Awad, S. S. & Berg, D. H. (2004) *J. Surg. Res.* 121, 92-100.
46. Owens, G. K., Kumar, M. S., Wamhoff, B. R. (2004) *Physiol. Rev.* 84, 767-801.
47. He, T.-C. et al. (1998) *Proc. Natl. Acad. Sci. USA* 95, 2509-2514.
48. Bonifacino, J. S. et al. eds. (1998) *Current Protocols in Cell Biology*, Chapter 8, Cell Cycle Analysis, John Wiley, New York).
49. Koppe, M. J. et al., (2004) *J. Nucl. Med.* 45, 1224-1232.
50. Rigney D R, Wei J Y. (2004) Note on the dispersion of generations among cells in senescing diploid fibroblast populations. *Mech. Ageing Dev.* 47, 187-197.

All cited patents, patent documents, and other references are hereby incorporated by reference.

What is claimed is:

1. An isolated nucleic acid comprising a p49/STRAP gene and adapted to express a p49/STRAP protein from the p49/STRAP gene in a recombinant host cell; wherein the p49/STRAP gene encodes a protein at least 90% identical to SEQ ID NO:1 or at least 90% identical to SEQ ID NO:2.

2. The isolated nucleic acid of claim 1 wherein the p49/STRAP gene encodes a protein at least 90% identical to SEQ ID NO:2.

3. The isolated nucleic acid of claim 1 wherein the p49/STRAP gene encodes a protein at least 90% identical to SEQ ID NO:1.

* * * * *